(12) United States Patent
Newman et al.

(10) Patent No.: US 8,748,608 B2
(45) Date of Patent: Jun. 10, 2014

(54) 4-PHENYLPIPERAZINE DERIVATIVES WITH FUNCTIONALIZED LINKERS AS DOPAMINE $D_3$ RECEPTOR SELECTIVE LIGANDS AND METHODS OF USE

(75) Inventors: Amy Hauck Newman, Phoenix, MD (US); Peter Grundt, Duluth, MN (US); George C. Cyriac, Severna Park, MD (US); Robert Luedtke, Fort Worth, TX (US); Jianjing Cao, Ellicott City, MD (US)

(73) Assignees: The United States of America as Represented by the Secretary of the Department of Health and Human Services, Washington, DC (US); The University of North Texas Health Science Center at Fort Worth, Fort Worth, TX (US)

( * ) Notice: Subject to any disclaimer, the term of this patent is extended or adjusted under 35 U.S.C. 154(b) by 608 days.

(21) Appl. No.: 12/664,668

(22) PCT Filed: Jun. 15, 2007

(86) PCT No.: PCT/US2007/071412
§ 371 (c)(1),
(2), (4) Date: Jun. 25, 2010

(87) PCT Pub. No.: WO2008/153573
PCT Pub. Date: Dec. 18, 2008

(65) Prior Publication Data
US 2010/0267737 A1    Oct. 21, 2010

(51) Int. Cl.
| | | |
|---|---|---|
| *C07D 213/56* | (2006.01) | |
| *C07D 209/42* | (2006.01) | |
| *C07D 295/145* | (2006.01) | |
| *C07D 295/15* | (2006.01) | |
| *C07D 307/85* | (2006.01) | |

(52) U.S. Cl.
USPC ........... 544/360; 544/373; 544/376; 544/379; 544/393

(58) Field of Classification Search
None
See application file for complete search history.

(56) References Cited

U.S. PATENT DOCUMENTS

| | | | |
|---|---|---|---|
| 8,119,642 B2 | 2/2012 | Newman et al. | |
| 2005/0197343 A1* | 9/2005 | Gmeiner et al. | ......... 514/252.13 |
| 2006/0106030 A1 | 5/2006 | Newman et al. | |
| 2010/0068138 A1 | 3/2010 | Newman et al. | |

FOREIGN PATENT DOCUMENTS

| | | |
|---|---|---|
| WO | 97-34889 A | 9/1997 |
| WO | 9731916 A | 9/1997 |
| WO | 9806717 A | 2/1998 |
| WO | 2004004729 A | 1/2004 |
| WO | 2004024878 A | 3/2004 |
| WO | 2006015737 A | 2/2006 |
| WO | 2006050976 A | 5/2006 |
| WO | 2006072608 A | 7/2006 |

OTHER PUBLICATIONS

International Search Report; International Application No. PCT/US2007/071412; Date of Completion of International Search Mar. 3, 2008 (5 pages).
Grundt, P. et al. 'Novel Heterocyclic trans Olefin Analoges of N-{4-[4-(2,3-Dichlorophenyl)piperazin-I-yl]butyl}arylcarboxamides as Selective Probe with High Affinity for the Dopamine D3 receptor.' J. Med. Chem. 2005, vol. 48, No. 3, pp. 839-848, ISSN 0022-2623 (10 pages).
Newman, A. H. et al. 'N-{4-[4-(2,3-Dichlorophenyl)piperazin-I-yl]butyl, Butenyl and Butynyl}arylcarboxamides as Novel Dopamine D3 Receptor Antagonits' Bioorganic & Medicinal Chemistry Letter 2003, vol. 13, No. 13, pp. 2179-2183 (5 pages).

* cited by examiner

*Primary Examiner* — Emily Bernhardt
(74) *Attorney, Agent, or Firm* — Cantor Colburn LLP

(57) ABSTRACT

Dopamine $D_3$ receptor antagonists and partial agonists are known to modulate the reinforcing and drug-seeking effects induced by cocaine and other abused substances. By introducing functionality into the butylamide linking chain of the 4-phenylpiperazine class of ligands, improved $D_3$ receptor affinity and selectivity, as well as water solubility, is achieved. A series of linking-chain derivatives are disclosed wherein functionality such as OH or OAc groups have been introduced into the linking chain. In general, these modifications are well tolerated at $D_3$ receptors and achieve high selectivity over $D_2$ and $D_4$ receptors.

18 Claims, 3 Drawing Sheets

Synthesis of the 3-hydroxyl amines 27[a]

[a] Reagents and conditions: (a) phthalimid potassium salt, DMF, microwave, 100 °C, 20 min; (b) 1-(2,3-dichlorophenyl)- or 1-(2-methoxyphenyl)-piperazine, 2-PrOH, microwave, 90 °C, 20 min; (c) hydrazine, ethanol, microwave, 90 °C, 20 min.

Synthesis of the 2-hydroxyl amines 30 [a]

[a] Reagents and conditions: (a) 1-(2,3-dichlorophenyl)- or 1-(2-methoxyphenyl)-piperazine, potassium carbonate, acetone, reflux, 24 h; (b) sodium azide, ammonium chloride, DMF, 100 °C; 4 h; (c) triphenyl phosphine, THF, room temperature, 16 h.

Synthesis of Compounds 9-23 and 34-49[a]

[a] Reagents and conditions: (a) CDI, pyridine or DCC, HOBt, DMF. 13 was prepared from N-(4-(4-(2,3-dichlorophenyl)piperazin-1-yl)but-2-enyl)-4-(pyridin-2-yl)benzamide; PG01037 by N-oxidation (mCPBA, CH$_2$Cl$_2$, room temperature, 16 h). 20 was prepared from 16 by acetylation (NEt$_3$, CH$_3$COCl, room temperature, 16 h).

4-PHENYLPIPERAZINE DERIVATIVES WITH FUNCTIONALIZED LINKERS AS DOPAMINE $D_3$ RECEPTOR SELECTIVE LIGANDS AND METHODS OF USE

BACKGROUND

The dopamine receptor system plays a key role in numerous neuropsychiatric and neurological disorders and investigation into mechanistic underpinnings and neuroadaptations within this family of receptors has been the focus of intensive research over the past decade. The dopamine $D_3$ receptor subtype has been hypothesized to play a fundamental role, for example, in the abuse-related effects of cocaine and other drugs of abuse. Hence, there is a well recognized need to develop novel, selective and bioavailable dopamine $D_3$ receptor ligands.

Further reasons for pursuing dopamine $D_3$ receptor selective ligands as medications for various conditions come from the brain localization of $D_3$ receptors, which are primarily expressed in limbic regions of the brain, including the nucleus accumbens. $D_3$ receptor blockade may attenuate drug reward and/or reinforcement while avoiding the risk of extrapyramidal side effects associated with the blockade of the more ubiquitous $D_2$ receptors.

The high degree of amino acid homology within the binding sites of the dopamine $D_2$-like receptors, and especially between the $D_2$ and $D_3$ dopamine receptor subtypes, has provided a formidable challenge in the pursuit to discover dopamine $D_3$-selective compounds. Thus far, high dopamine $D_2/D_3$ selectivity has generally been achieved with relatively large molecules, characterized, for example, by a heterocyclic moiety bridged by an unsubstituted 4-carbon chain, or carbocycle to an extended or substituted arylamide or a corresponding bioisotere.

In addition to optimizing pharmacological selectivity, it is also important that dopamine $D_3$-selective compounds be able to penetrate the blood brain barrier (BBB) and have appropriate pharmacokinetics to facilitate interpretation of in vivo results. However, generally relatively high doses of $D_3$-selective agents have been required for behavioral activity. It is not known whether these required high doses are due to a low permeability surface area product of these agents for crossing the BBB, high peripheral metabolism, large uptake in some other organ or compartment, or is due to some other reason.

Therefore, there is a well recognized need in the art for highly $D_3$-selective compounds that are able to penetrate the blood brain barrier, and that show activity at relatively low dosages.

DESCRIPTION OF THE INVENTION

Figure 1:
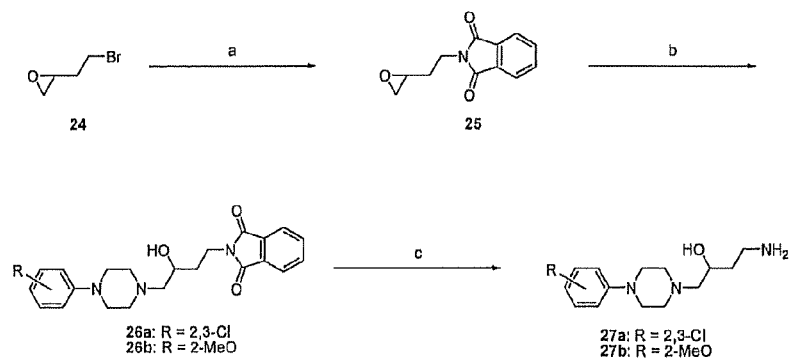
FIG. 1: Synthesis of the 3-hydroxylamines 27.

The present invention relates to chemical compounds of the following chemical formula:

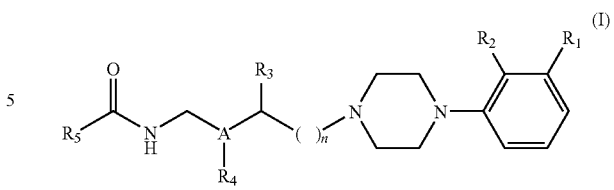

wherein
A=$CHR_4$ or trans CH=CH;
n=0 or 1;
$R_1$ and $R_2$=independently represent hydrogen, halogen, or alkoxy;
$R_3$ or $R_4$=H, OH, OAc, alkoxy, halogen, amino, nitro, alkoxy, alkyl, acyl and or pyridyl;
$R_5$=phenyl, indole, thiophene, benzofuran, fluorenyl, or 2-pyridylphenyl; and $R_5$ is optionally substituted with one or more of hydrogen, halogen, amino, nitro, hydroxyl, alkoxy, alkyl, acyl and pyridyl, substitution may occur at any of the ortho, meta, or para positions; including all enantiomers and pharmaceutical salts.

In particular, when $R_3$ and $R_4$ are not H, chiral centers are present on the butyl amide linking chain and are included within the scope of the invention.

In one embodiment of the invention A in Formula (I) is C.

In one embodiment, the present invention is directed to compounds of the following chemical formula:

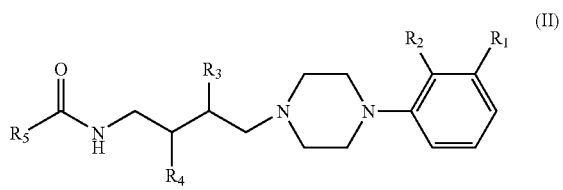

Wherein
$R_1$ and $R_2$=2-methoxy or 2,3-dichloro;
|$R_3$ or $R_4$=OH, OAc, H; and|
$R_5$=indole, thiophene, benzofuran, fluorenyl, or 2-pyridylphenyl, and $R_5$ is substituted with one or more of methoxy, fluoro, or iodo;
including all enantiomers and pharmaceutical salts.

Dopamine $D_3$ receptor antagonists and partial agonists are known to modulate the reinforcing and drug-seeking effects induced by cocaine and other abused substances. The introduction of functionality into the butylamide linking chain of the 4-phenylpiperazine class of ligands, improves $D_3$ receptor affinity and selectivity, as well as water solubility. See *J. Med. Chem.* 2005, 48, 839-848. Along these lines, a series of linking-chain derivatives wherein functionality such as OH, OAc, etc., are introduced into the linking chain is disclosed.

In general, these modifications are well tolerated at $D_3$ receptors ($K_i$=<1-5 nM) and several analogues demonstrated >100-fold selectivity over $D_2$ and $D_4$ receptors using competition binding assays in HEK 293 cells transfected with either $hD_{2L}$, $hD_3$ or $hD_4$ dopamine receptors. Furthermore, addition of these groups affected efficacy of the compounds as measured by quinpirole stimulation of mitogenesis at human dopamine $D_3$ receptors transfected into Chinese hamster ovary (CHO) cells. These compounds also provide additional tools with which to elucidate the role of $D_3$ receptors in drug reinforcement in vivo.

The dopamine $D_3$ receptor subtype is a member of the dopamine $D_2$ family of receptors. These receptors are involved in a number of CNS disorders including but not limited to psychostimulant abuse, psychosis and Parkinson's disease, (Newman, A. H.; Grundt, P.; Nader, M. A., *Dopamine D3 receptor partial agonists and antagonists as potential drug abuse therapeutic agents*. J. Med. Chem. 2005, 48, 3663-3679.; Heidbreder, C. A.; Andreoli, M.; Marcon, C.; Thanos, P. K.; Ashby, C. R.; Gardner, E. L., *Role of dopamine D-3 receptors in the addictive properties of ethanol*. Drugs Today 2004, 40, 355-365.; Joyce, J. N.; Milian, M. J., *Dopamine D-3 receptor antagonists as therapeutic agents*, Drug Discov. Today 2005, 10, 917-925; See also, Le Foil, B.; Goldberg, S. R.; Sokoloff, P., *The dopamine D-3 receptor and drug dependence: Effects on reward or beyond?* Neuropharmacology 2005, 49, 525-541; Luedtke, R. R.; Mach, R. H., *Progress in developing D3 dopamine receptor ligands as potential therapeutic agents for neurological and neuropsychiatric disorders* Curr. Pharm. Design 2003, 9, 643-671; Boeckler, F.; Gmeiner, P., *The structural evolution of dopamine D-3 receptor ligands: Structure-activity relationships and selected neuropharmacological aspects* Pharmacol. Ther. 2006, 112, 281-333.)

Compounds that bind with high affinity and selectivity to $D_3$ receptors not only provide important tools with which to study the structure and function of this receptor subtype, but also have a therapeutic effect in the treatment of numerous psychiatric and neurologic disorders.

It is known in the art that the $D_2$ family of receptors (which includes $D_3$) are increased in cocaine addicts and monkeys trained to self administer cocaine. See Volkow, N. D.; Wang, G. J.; Fowler, J. S.; Logan, J.; Gatley, S. J.; Wong, C.; Hitzemann, R.; Pappas, N. R., *Reinforcing effects of psychostimulants in humans are associated with increases in brain dopamine and occupancy of D-2 receptors*, J. Pharmacol. Exp. Ther. 1999, 291, 409-415; Volkow, N. D.; Fowler, J. S.; Wang, G. J.; Swanson, J. M., *Dopamine in drug abuse and addiction: results from imaging studies and treatment implications*, Mol. Psychiatry. 2004, 9, 557-569; Nader, M. A.; Morgan, D.; Gage, H. D.; Nader, S. H.; Calhoun, T. L.; Buchheimer, N.; Ehrenkaufer, R.; Mach, R. H., *PET imaging of dopamine $O_2$ receptors during chronic cocaine self-administration in monkeys*, Nat. Neurosci. 2006, 9, 1050-1056.

The 4-phenylpiperazine derivatives are an important class of dopamine $D_3$ selective ligands. However, due to their highly lipophilic nature, these compounds often suffer from solubility problems in aqueous media and reduced bioavailability. To address these problems, functionality (e.g. OH, OCH3, OAc, etc.,) is introduced into the carbon chain linker of these compounds. Compared to currently available dopamine $D_3$ receptor ligands, the resulting compounds show improved pharmacological properties and $D_3$ selectivities, but due to their more hydrophilic nature these derivatives also have improved water solubility and bioavailability.

The more hydrophilic nature of these derivatives is shown by the cLogP (calculated measure of lipophilicity) and polar surface areas (PSA). See Table 1. As expected, the introduction of a hydroxyl group into the butyl linking chain resulted in lower clogP values, showing decreased lipophilicity, compared to the corresponding parent olefinic or aliphatic compounds. The calculated polar surface area (PSA) was significantly increased (by 20 $Å^2$). Values less than 75 $Å^2$ are considered as being favorable for brain penetration. See Grundt, P.; Prevatt, K. M.; Cao, J.; Taylor, J.; Floresca, C. Z.; Choi, J.-K.; Jenkins, B. G.; Luedtke, R. R.; Newman A. H. *Heterocyclic Analogues of N-(4-(4-(2,3-Dichlorophenyl)piperazin-1-yl)-butyl)-aryl-carboxamides with Functionalized Linking Chains as Novel Dopamine D3 Receptor Ligands: Potential Substance Abuse Therapeutic Agents*. J. Med. Chem. 2007, in press.

According to Lipinski's "rule of 5" cLogP values in the 2-5 range are expected to have drug like properties. See Lipinski, C. A., *Drug-like properties and the causes of poor solubility and poor permeability*, J. Pharmacol. Toxicol. Methods 2000, 44, 235-249. Comparisons of the hydroxylated analogues with their saturated butyl or olefinic counterparts demonstrate that both PSA and particularly cLogP values are predictive of improved "drug-like", soluble, bioavailable and CNS penetrant profiles. The PSA values were calculated according to Ertl, P.; Rohde, B.; Selzer, P., Fast, *Calculation of molecular polar surface area as a sum of fragment-based contributions and its application to the prediction of drug transport properties,* 2000, 43, 3714-3717. CLogP values were calculated using *Cambridgesoft ChemDraw Ultra* 9.0, 2004.

Based on their neurochemical and behavioral properties, the dopamine $D_3$ receptor selective ligands of the present invention are useful in methods for the treatment of all addictions, especially including nicotine and alcohol, and psychostimulant abuse, such as of cocaine, amphetamine, and derivatives thereof. The dopamine $O_3$ receptor selective ligands of the present invention are also useful in the treatment of schizophrenia and Parkinson's disease and dyskinesias associated with these disorders and treatment thereof. Generally the methods involve administering a pharmaceutically effective amount of a compound of the present invention to a patient in need thereof.

$D_3$ selectivity is expressed as $D_2/D_3$; a ratio that is derived from the $K_i$ value at $D_2$ over the $K_i$ value at $D_3$ receptors. Hence, a compound that exhibits higher affinity at $D_3$ than at $D_2$ receptors, has a $D_2/D_3$ ratio>1." See Newman, A. H.; Grundt, P.; Nader, M. A., *Dopamine D3 receptor partial agonists and antagonists as potential drug abuse therapeutic agents*, J. Med. Chem. 2005, 48, 3663-3679.

The term "pharmaceutically effective amount" as used herein means an amount of the compound that produces any therapeutic effect or imaging effect in a patient. Therapeutic effect in a patient preferably relates to one of the above-mentioned conditions.

The term "alkyl" is used herein to refer to a branched or unbranched, saturated or unsaturated, monovalent hydrocarbon radical having from 1-8 carbons, including arylalkyls. Suitable alkyl radicals include, for example, methyl, ethyl, n-propyl, i-propyl, 2-propenyl (or allyl), n-butyl, t-butyl, i-butyl (or 2-methylpropyl), amyl, n-amyl, hexyl, etc. As used herein, the term alkyl encompasses "substituted alkyls." The term "substituted alkyl" refers to alkyl as just described including one or more functional groups such as lower alkyl, aryl, aralkyl, acyl, halogen (i.e., alkylhalos, e.g., $CF_3$), hydroxyl, amino, acylamino, acyloxy, alkoxyl, mercapto and the like. These groups may be attached to any carbon atom of the lower alkyl moiety.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy, etc.

The term "lower alkyl" means $C_1$ to $O_3$. The term "halogen" is used herein to refer to fluorine, bromine, chlorine, and iodine atoms. The term "hydroxyl" is used herein to refer to the group —OH.

As used herein, "psychostimulant abuse" has its conventional meaning, i.e., misuse or addiction of a psychostimulant, such as cocaine, amphetamine and derivatives thereof. Typically, cocaine is taken by a person due to a craving for cocaine generated by its prior use. Cocaine is abused when it is used for gratification, producing effects not required or recommended for therapy. The resultant high use of cocaine produces many serious and adverse side effects. As such, it is highly desirable to reduce the number and/or intensity of episodes in which a person experiences a craving for the substance or, more preferably, to eliminate the craving episodes entirely. Dopamine $D_3$ antagonists or partial agonists have demonstrated utility in reducing craving in animal models (Pilla, M. et al. Nature 400:371-375 (1999), Vorel, S. R. et al. J. Neurosci. 22:9595-9603 (2002), DiCiano, P. et al. Neuropsychopharmacology 28:329-338 (2003)).

"Treatment" or "treating," as used herein, refers to any administration of a compound of the present invention and includes: (i) inhibiting the symptoms of the disease, e.g., cocaine addiction; and/or (ii) lessening or inhibiting the long term effects of the disease, e.g., cocaine addiction. In therapeutic applications, compositions are administered to a patient already suffering from the disease, e.g., cocaine addiction or Parkinson's disease, in a pharmaceutically effective amount.

In conjunction with the foregoing method, the present invention provides pharmaceutical compositions comprising a compound disclosed herein and a pharmaceutically acceptable diluent, carrier or excipient. While it is possible to administer the active ingredient of this invention alone, it is preferable to present it as part of a pharmaceutical formulation. The formulations of the present invention comprise at least one compound described herein in a therapeutically or pharmaceutically effective dose together with a pharmacologically or therapeutically acceptable carrier. The phrase "pharmaceutically or therapeutically acceptable carrier," as used herein, refers to a carrier medium which does not interfere with the effectiveness of the biological activity of the active ingredients, especially $D_3$ receptor binding of a compound of the present invention, and which is not toxic to the host or patient.

The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred form will depend on the particular therapeutic application at hand. The methods for the formulation and preparation of therapeutic compositions comprising the compounds of the invention are well known in the art and are described in, for example, REMINGTON'S PHARMACEUTICAL SCIENCES (Mack Publishing Company, Philadelphia, Pa., 17th ed. (1985)), THE MERCK INDEX 11th Ed., (Merck & Co. 1989), and Langer, Science 249: 1527-1533 (1990), the teachings of which are incorporated herein by reference.

For parenteral administration, for example, the pharmaceutical compositions comprise a solution of a compound of the present invention, as described above, dissolved or suspended in an acceptable carrier, preferably an aqueous carrier. A variety of aqueous carriers can be used including, for example, water, buffered water, 0.4% saline, 0.3% glycine, hyaluronic acid and the like. These compositions may be sterilized by conventional, well-known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally about 1% to 95%, preferably 10% to about 95% of the active ingredient and, more preferably, about 25% to about 75% of the active ingredient.

For aerosol administration, the compounds of the present invention are preferably supplied in a finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included as desired, as with, e.g., lecithin, for intranasal delivery.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the compounds of the present invention will be in the range of 0.05 to 1000 milligram (mg) per recipient per day, preferably in the range of 0.1 to 100 mg per day. The desired dosage is preferably presented in one, two, three, four or more subdoses administered at appropriate intervals throughout the day. These subdoses can be administered as unit dosage forms, for example, containing 0.01 to 1000 mg, preferably 0.01 to 100 mg of active ingredient per unit dosage form. Again, the desired dosage will depend on, for example, the particular compound employed, the disease to be treated, the manner of administration, the weight and general state of health of the patient, and the judgment of the prescribing physician.

Based on their neurochemical and behavioral properties, the $D_3$ receptor selective ligands of the present invention are also useful as imaging probes. The present compounds may be useful for functional MRI imaging of D3 receptors. In addition, the dopamine $D_3$ receptor selective ligands of the present invention are useful as imaging agents for dopamine $D_3$ receptors and as imaging probes for neurodegenerative disorders (e.g., Parkinson's disease). As such, in another aspect, the present invention provides a method of selectively imaging dopamine binding sites of the central nervous system of a subject, such as the brain of a human patient, the method comprising:

(a) administering to a human in need thereof an inventive compound of the present invention; and (b) detecting the binding of the compound to the central nervous system tissue, such as the dopamine $D_3$ receptors in the brain.

Moreover, in yet another aspect, the present invention provides a method for detecting or monitoring a disease resulting from abnormal distribution and/or density of dopamine $D_3$ receptor in the central nervous system of a subject, comprising:

(a) administering to the subject a detectably labeled compound of the invention;

(b) detecting the binding of that compound to dopamine $D_3$ receptor in the central nervous system;

(c) determining the distribution and/or density of the dopamine $D_3$ receptor in the central nervous system tissue;

(d) comparing the distribution and/or density obtained in (c) with the distribution and/or density of dopamine $D_3$ receptor in a corresponding normal tissue; and (e) diagnosing a disease state by a difference in the distribution and/or density between the normal tissue and the subject tissue.

In a presently preferred embodiment, the dopamine selective ligands of the present invention are labeled with a radioactive label using standard labeling techniques known to and used by those of skill in the art. Suitable labels include, but are not limited to: $^{123}I$, $^{11}C$, $^{18}F$, or $^{99}Tc$. In addition, binding of the dopamine $D_3$ receptor selective ligands to the brain, such as limbic brain regions, including the Nucleus Accumbens and islands of Calleja, is detected using methods known in the art, such as positron emission tomography (PET), single-photon emission computed tomography (SPECT), or magnetic resonance imaging (MRI). (See, e.g., Yokoi F. et al., *Neuropsychopharmacology* 27(2):248-59 (2002); Pilowsky L. S., *Nucl Med Commun* 22(7):829-33 (2001); Soares J C and Innis R B, *Biol Psychiatry* 46(5):600-15 (1999); and Videbaek C, *J Cereb Blood Flow Metab* 21(1):92-7 (2001), the teachings of which are incorporated herein by reference.

Preferably SPECT imaging employs gamma-emitting derivatives of the ligands described herein (e.g., dopamine $D_3$ receptor selective ligands labeled with $^{123}I$ or $^{99}Tc$). Yokoi et al. (supra) have mapped the normal distribution of dopamine $D_2$ and $D_3$ receptors in humans. Using this method, one can diagnose and/or monitor neurodegenerative disorders, such as Parkinson's disease, characterized by the progressive degeneration of dopamergic nerve terminals.

EXAMPLES

All melting points were determined on a Thomas-Hoover melting point apparatus and are uncorrected. The $^1H$ and $^{13}C$ NMR spectra were recorded on a Varian Mercury Plus 400 instrument. Proton chemical shifts are reported as parts per million ($\delta$ ppm) relative to tetramethylsilane (0.00 ppm) as an internal standard. Coupling constants are measured in hertz (Hz). Chemical shifts for $^{13}C$ NMR spectra are reported as $\delta$ relative to the deuterium signal of the solvent ($CDCl_3$, 77.5 ppm, $CD_3OD$ 49.3). Microanalyses were performed by Atlantic Microlab, Inc. (Norcross, Ga.) and agree within 0.4% of calculated values. If not stated otherwise all final compounds were purified by column chromatography (silica gel, Merck, 230-400 mesh, 60 Å) or thin layer chromatography (silica gel, Analtech, 1000 micron) using $EtOAc/CHCl_3/MeOH$ 5:5:1, 1% triethylamine or $CHCl_3/MeOH$ 10:1, 1% triethylamine as an eluent. Microwave reactions were performed in a CEM Discover Labmate system equipped with a 80 mL pressure vessel. Yields and reaction conditions are not optimized. Generally, yields and spectroscopic data refer to the free base.

Methods for performing in vitro dopamine receptor binding studies are described in Huang et al. *J. Med. Chem.* 44:1815-1826 (2001) and Luedtke et al. *Synapse* 38:438-439 (2000), the contents of which are hereby incorporated by reference. These papers describe radioactively labeled dopamine receptor selective ligands binding with picomolar affinity and nonselectivity to $D_2$ and $D_3$ dopamine receptors expressed in Sf9 and HEK 293 cells. $^{125}I$-IABN binds with 7- to 10-fold lower affinity to human D4.4 dopamine receptors expressed in HEK 293 cells. Dissociation constants (Kd) calculated from kinetic experiments were found to be in agreement with equilibrium Kd values obtained from saturation binding studies. Saturation plots of the binding of $^{125}I$-IABN with rat caudate membrane preparations were monophasic and exhibited low nonspecific binding. The pharmacologic profile of the binding of $^{125}I$-IABN to rat caudate was found to be consistent with a $D_2$-like receptor, suggesting that in the caudate the ligand binds primarily to $D_2$ dopamine receptors. IABN was found to bind with low affinity to σ1 and σ2 binding sites, as well as to $D_{1a}$ dopamine receptors. Quantitative autoradiographic studies using rat brain indicated that $^{125}I$-IABN selectively labels the striatum and the olfactory tubercle area, which is consistent with the labeling receptors expressed in HEK cells. Therefore, $^{125}I$-IABN appears to be a high affinity, selective antagonist at $D_2$-like dopamine receptors.

Human dopamine $D_2$-long ($D_2$) and $D_3$ ($D_3$) receptors were expressed in HEK cells. In brief, stably transfected HEK cells expressing the human $D_2$-long and the $D_3$ dopamine receptor were developed using the pIRES bicistronic expression vector (CLONTECH; Palo Alto, Calif.). The level of expression of $D_2$ or $D_3$ receptors was determined to be greater than 2,000 fmoles/mg protein. For comparison, human dopamine $D_4$ ($D_4$) receptors were obtained from HEK 293 cells stably transfected with a PCR product of a human cDNA coding for the D4.4 form of the human $D_4$ dopamine receptor. The density of binding sites is approximately 1000 fmol/mg protein.

To measure $D_2$ and $D_3$ stimulation of mitogenesis (agonist assay) or $D_2$ and $D_3$ inhibition of quinpirole stimulation of mitogenesis (antagonist assay), CHOp-cells (human receptor) were seeded in a 96-well plate at a concentration of 5,000 cells/well. The cells were incubated at 37° C. in α-MEM with 10% FBS, 0.05% penicillin-streptomycin, and 200 μg/mL of G418. After 48 hours, the cells were rinsed twice with serum-free α-MEM and incubated for 24 hours at 37° C. In the functional assay for agonism, the medium was removed and replaced with 90 μl of serum-free α-MEM and 10 μl of test compound in sterile water; in the antagonist assay, the test compound was diluted in sterile water plus 30 nM quinpirole. After another 24-hour incubation at 37° C., 0.25 μCi of [$^3H$] thymidine was added to each well and the plates were further incubated for 2 hours at 37° C. The cells were then trypsinized, and the plates were filtered and counted as usual in the art. Quinpirole was run on every plate as an internal standard.

The procedures to determine the binding affinities at the human dopamine $D_2$-like receptors, the binding affinities at the serotonin $5HT_{1A}$, $5HT_{2A}$ and $5HT_{2c}$ receptors and functional mitogenesis assay are known in the art. See *J. Med. Chem.* 2005, 48, 839-848. See also, *NIDA Research Monograph #178, Proceedings of the College of Drug Dependence*, p. 440-466, 1998. Both of these references are incorporated by reference.

Figure 2:
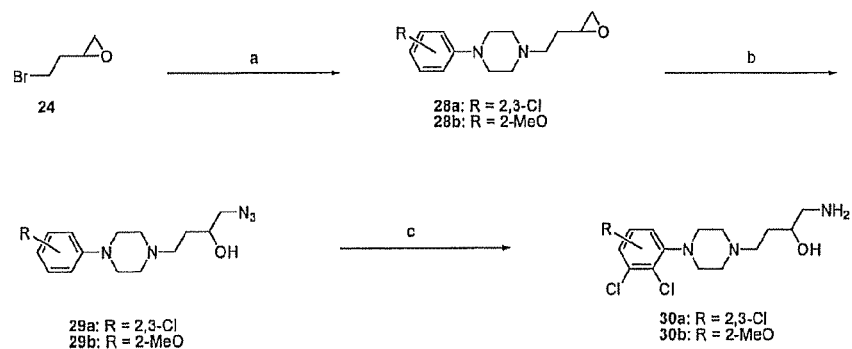
FIG. 2: Synthesis of the 2-hydroxylamines 30.

The racemic hydroxybutyl amine intermediates needed to prepare the 3-hydroxy derivatives 16-19 and 2-hydroxy analogues 21-23 were synthesized as depicted in FIGS. 1 and 2. In both cases, the synthetic routes used bifunctional 2-(2-bromoethyl)oxirane as starting material. See Cruickshank, P. A.; Fishman, M., "Studies In Alkylation.2. Reactions Of Epoxyalkyl Bromides", *J. Org. Chem.* 1969, 34, 4060-4065, incorporated by reference. All key steps were found to be regioselective and only the products depicted were isolated. The amines (FIG. 1) were synthesized via a modified Gabriel synthesis. No side products were observed in the alkylation reaction to form the phthalimide.

Figure 3:
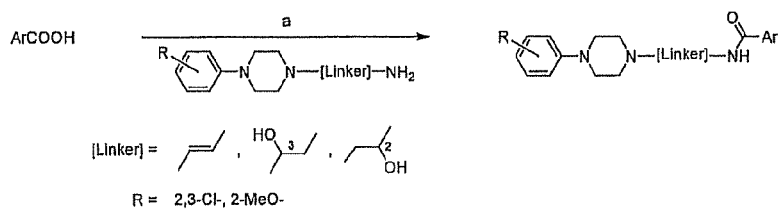
FIG. 3: Synthesis of Compounds 2-23.

The opening of the oxirane moiety occurred selectively at the least substituted side to yield the 3-hydroxy phthalimides, which were then deprotected with hydrazine to afford the hydroxylamines. In the case of the 2-hydroxy amines (30, FIG. 2) the butylpiperazine bond was formed first, followed by a regioselective opening of the epoxide with sodium azide and a Schlesinger-type reduction. The general reaction sequence used to prepare the dopamine $D_3$ receptor preferring analogues 2-23 incorporating a butyl, butenyl or hydroxybutyl linking chain as depicted in FIG. 3. The required carboxylic acids were prepared according to procedures known in the art. See *J. Med. Chem.* 2001, 44, 3175-3186. See also, Synlett 2000, 829-831. Both of these references are incorporated by reference.

The general synthesis of the butyl amines and the butenyl amines is also known in the art. See *J. Med. Chem.* 2005, 48, 839-848; *J. Med. Chem.* 2001, *J. Med. Chem.* 2003, 46, 3883-3899; and *Bioorg. Med. Chem. Lett.* 2003, 13, 2179-2183. All of these references are incorporated by reference.

General procedure for the synthesis of carboxylic acid amides. The 1-imidazole adduct appropriate carboxylic acid was reacted with the suitable secondary amine derivative as known in the art. See *J. Med. Chem.* 2005, 48, 839-848, incorporated by reference. The crude product was purified by chromatography, structurally characterized and then converted into its oxalate or hydrochloride for biological evaluation.

Example 1

|N-(4-(4-(2-Methoxyphenyl)piperazin-1-yl)butyl)-9H-fluorene-2-carboxamide (7). Prepared from 9H-fluorene-2-carboxylic acid and 4-(4-(2-methoxyphenyl)-piperazin-1-yl)-butylamine according to the general procedure. Yield: 74%. Mp. (hydrochloride): 208-210° C. $^1$H NMR (CDCl$_3$): δ 1.67-1.73 (m, 4H), 2.47 (t, J 6.7, 2H), 2.65 (s, 4H), 3.04 (s, 4H), 3.51 (q, J 6.1, 2H), 3.84 (s, 3H), 3.91 (s, 2H), 6.82-6.88 (m, 4H), 698 (dt, J 7.8, 4.6, 1H), 7.35 (td, J 7.4, 1.2, 1H), 7.40 (t, J 7.0, 1H), 7.55 (d, J 7.0, 1H), 7.75-7.77 (m, 2H), 7.81 (d, J 8.0, 1H), 7.96 (s, 1H). $^{13}$C NMR (CDCl$_3$): δ 25.0, 27.9, 37.3, 40.5, 50.93, 53.9, 55.8, 58.5, 111.5, 118.6, 120.1, 121.0, 121.4, 123.4, 124.4, 125.6, 126.3, 127.4; 128.0; 141.2, 141.6, 143.8, 144.4, 145.1, 152.7, 168.6. Anal. (C$_{29}$H$_{33}$N$_3$O$_2$.2HCl. 0.5H$_2$O) C, H, N.

Example 2

N-(4-(4-(2-Methoxy-phenyl)-piperazin-1-yl)-butyl)-4-pyridin-2-yl-benzamide (8). Prepared from 4-pyridin-2-yl-benzoic acid hydrochloride and 4-(4-(2-methoxy-phenyl)-piperazin-1-yl)-butylamine according to the general procedure. Yield: 53%. Mp. (oxalate): foam. $^1$H NMR (CDCl$_3$): δ1.67-1.74 (m, 4H), 2.49 (t, J 6.84, 2H), 2.67 (s, 2H), 3.07 (s, 2H), 3.51 (q, J 6.0, 2H), 3.84 (s, 3H), 6.83 (m, 5H), 7.26 (m, 1H), 7.73-7.79 (m, 2H), 7.89 (d, J 8.2, 2H), 8.06 (d, J 8.6, 2H), 8.71 (dt, J 4.7, 1.3, 1H). $^{13}$C NMR (CDCl$_3$): δ 24.8, 27.9, 40.4, 50.8, 53.9, 55.8, 58.5, 111.6, 118.7, 121.3, 121.4, 128.1, 123.4, 127.4, 127.9, 135.6, 137.3, 142.5, 150.3, 152.7, 156.7, 167.8. Anal. (C$_{27}$H$_{32}$N$_4$O$_2$.(COOH)$_2$. 0.75H$_2$O) C, H, N.|

Example 3

N-(4-(4-(2,3-Dichloro-phenyl)-piperazin-1-yl)-trans-but-2-enyl)-4-(6-oxo-1,6-dihydro-pyridin-2-yl)-benzamide (9).

A suspension of 0.12 g (0.53 mmol) 4-(6-oxo-1,6-dihydro-pyridin-2-yl)-benzoic acid, 0.13 g (0.64 mmol) dicyclohexylcarbodiimide, 0.1 g (0.7 mmol) 1-hydroxybenzotriazole hydrate in 15 mL DMF was treated at 0° C. with 0.16 g (0.53 mmol) 4-(4-(2,3-chloro-phenyl)-piperazin-1-yl)-trans-but-2-enyl amine and 0.17 mL (1.2 mmol) triethylamine. The reaction mixture was stirred at room temperature for 3 days and filtered. The solvent was removed in vacuo and the residue was taken up in saturated sodium bicarbonate and CHCl$_3$. The combined organics were dried with sodium sulphate, concentrated and the crude product was purified by thin layer chromatography. Yield: 0.10 g (38%). Mp. (oxalate): 153-154° C. $^1$H NMR (CDCl$_3$): δ 2.67 (s, 4H), 3.06 (s, 6H), 4.11 (m, 2H), 5.74-5.83 (m, 2H), 6.51-6.54 (m, 2H), 6.70 (t, J 5.3, 1H), 6.95 (dd, J 6.7, 2.9, 1H), 7.11-7.17 (m, 2H), 7.50 (dd, J 9.1, 7.0, 1H), 7.72 (d, J 8.3, 2H), 7.85 (d, J 8.4, 2H). $^{13}$C NMR (CDCl$_3$): 40.6, 50.2, 52.3, 59.4, 105.9, 17.9, 118.1, 124.1, 126.3, 126.6, 126.7, 127.0, 127.3, 130.2, 133.2, 135.0, 135.7, 141.6, 145.6, 150.4, 164.5, 167.0. Anal. (C$_{26}$H$_{26}$Cl$_2$N$_4$O$_2$ 1.5 (COOH)$_2$) C, H, N.

Example 4

N-(4-(4-(2,3-Dichloro-phenyl)-piperazin-1-yl)-trans-but-2-enyl)-4-(6-methyl-pyridin-2-yl)-benzamide (10). Prepared from 4-(6-methylpyridin-2-yl)benzoic acid hydrochloride and 4-(4-(2,3-chloro-phenyl)-piperazin-1-yl)-trans-but-2-enyl amine according to the general procedure. Yield: 18%. Mp. (oxalate): 125-126° C. $^1$H NMR (CDCl$_3$): δ 2.63 (s, 7H), 3.08 (s, 6H), 4.12 (m, 2H), 5.78-5.80 (m, 2H), 6.42 (s, br, 1H), 6.95 (d, J 6.7, 2.7, 1H), 7.11-7.16 (m, 3H), 7.55 (d, J 7.7, 1H), 7.65 (t, J 7.6, 1H), 7.87 (d, J 8.7, 2H), 8.05 (d, J 8.3, 2H). $^{13}$CNMR (CDCl$_3$): δ 25.2, 42.0, 51.7, 53.7, 60.7, 118.3, 119.1, 122.8, 125.0, 127.5, 127.8, 127.9, 129.4, 130.2, 134.4, 134.7, 137.5, 143.1, 151.7, 156.0, 159.0, 167.4. Anal. (C$_{27}$H$_{28}$Cl$_2$N$_4$O).2(COOH)$_2$): C, H, N.

Example 5

N-(4-(4-(2,3-Dichlorophenyl)piperazin-1-yl)-trans-but-2-enyl)-4-(3-methyl-pyridin-2-yl)-benzamide (11). Prepared from 4-(3-methylpyridin-2-yl)benzoic acid hydrochloride and 4-(4-(2,3-chloro-phenyl)-piperazin-1-yl)-trans-but-2-enyl amine according to the general procedure. Yield: 55%. Mp. (oxalate): foam. $^1$H NMR (CDCl$_3$): δ 2.34 (s, 3H), 2.65 (s, 4H), 3.07-3.10 (m, 6H), 6.12 (m, 2H), 5.78-5.82 (m, 2H), 6.49 (t, J 5.5, 1H), 6.95 (dd, J 6.5, 2.9, 1H), 7.12-7.16 (m, 2H), 7.21 (dd, J 7.6, 4.8, 1H), 7.57-7.62 (m, 3H), 7.86 (dt, J 8.6, 2.0, 2H), 8.53 (dt, J 4.2, 0.8, 1H). $^{13}$C NMR (CDCl$_3$): δ 20.4, 42.0, 51.7, 53.7, 60.7, 119.1, 123.0, 125.0, 127.3, 127.9, 129.4, 129.7, 130.3, 131.4, 134.2, 134.4, 139.2, 144.1, 147.5, 151.6, 158.0, 167.5. Anal. (C$_{27}$H$_{28}$Cl$_2$N$_4$O.1.5(COOH)$_2$. 0.5C$_3$H$_7$OH.0.5H$_2$O) C, H, N.

Example 6

N-(4-(4-(2,3-Dichloro-phenyl)-piperazin-1-yl)-trans-but-2-enyl)-4-(pyridin-N-oxide-2-yl)-benzamide (12). Prepared from 4-(pyridin-N-oxide-2-yl)-benzoic acid and 4-(4-(2,3-dichloro-phenyl)-piperazin-1-yl)-trans-but-2-enylamine according to the general procedure. Yield: 27%. Mp. (oxalate): 153-154° C. $^1$HNMR (CDCl$_3$): δ 2.91 (s, br, 4H), 3.06 (m, 6H), 4.07 (m, 2H), 5.71-5.82 (m, 2H), 6.93-6.96 (m, 2H), 7.12-7.15 (m, 2H), 7.27-7.31 (m, 1H), 7.36 (t, J 7.54, 1H), 7.45 (d, J 7.83, 1.74, 1H), 7.86 (m, 4H), 8.33 (d, J 6.65, 0.78, 1H). $^{13}$C NMR (CDCl$_3$): δ 41.8, 51.4, 53.4, 60.4, 118.9, 124.8, 125.4, 126.5, 127.3, 127.7, 127.7, 128.9, 129.7, 130.3, 134.2, 135.5, 135.6, 140.7, 148.7, 151.39, 166.9. Anal. ($C_{26}H_{26}Cl_2N_4O_2$.1.5(COOH)$_2$): C, H, N.

Example 7

4-(2,3-Dichlorophenyl)-1-(4-(4-(pyridin-2-yl)benzamido)-trans-but-2-enyl)-piperazine 1-oxide (13). A solution of PG01037, see U.S. 2006/0106030 (288 mg, 0.60 mmol) in 10 mL dichloromethane was treated at 0° C. with meta-chloroperbenzoic acid (0.16 g, 77%, 0.72 mmol). After stirring for 16 h at room temperature, the reaction mixture was successively washed with saturated sodium bicarbonate solution, H$_2$O and brine and dried with sodium sulphate. The volatiles were removed in vacuo and the residue was purified by preparative thin layer chromatography. Yield: 93 mg (32%). Mp. (hydrochloride): foam. $^1$H NMR (CD$_3$OD): δ 3.23-3.29 (m, 4H), 3.50-3.61 (m, 4H), 3.99 (d, J 6.5, 1H), 4.13 (d, J 4.6, 1H), 6.04-6.18 (m, 2H), 7.18 (dd, J 7.8, 3.9, 1H), 7.24-7.28 (m, 2H), 7.40 (m, 1H), 7.91-7.93 (m, 2H), 7.99 (d, J 8.4, 2H), 8.06 (d, J 8.7, 2H), 8.64 (dt, J 4.8, 1.2, 1H). $^{13}$C NMR (CDCl$_3$): δ 41.0, 45.5, 63.5, 72.0, 119.3, 120.0, 121.6, 123.1, 125.4, 127.0, 127.3, 127.7, 128.0, 133.8, 134.6, 137.8, 137.9, 142.2, 149.3, 150.1, 156.4, 168.3. Anal. ($C_{26}H_{26}Cl_2N_4O_2$:2HCl.0.5H$_2$O) C, H, N.

Example 8

N-(4-(4-(2-Methoxy-phenyl)-piperazin-1-yl)-trans-but-2-enyl)-4-pyridin-2-yl-benzamide (14). Prepared from 4-pyridin-2-yl-benzoic acid hydrochloride and 4-(4-(2-methoxyphenyl)-piperazin-1-yl)-trans-but-2-enyl amine according to the general procedure. Yield: 65%. Mp. (hydrochloride): 168-170° C. $^1$H NMR (400 MHz, CDCl$_3$): δ 2.70 (s, 4H), 3.12 (s, 6H), 3.86 (s, 3H), 4.13 (m, 2H), 5.78-5.85 (m, 2H), 6.43 (m, 1H), 6.85-7.02 (m, 4H), 7.27 (s, 2H), 7.77 (s, 2H), 7.90 (d, J 7.5, 2H), 8.06 (d, J 8.1, 2H), 8.72 (d, J 3.1, 1H). $^{13}$C NMR (101 MHz, CDCl$_3$): δ 41.0, 50.9, 53.7, 55.8, 60.7, 111.6, 118.7, 121.3, 121.4, 123.2, 123.5, 127.5, 127.9, 129.1, 130.5, 135.0, 137.4, 141.6, 142.7, 150.3, 152.7, 156.7, 167.4. Anal. ($O_{27}H_{30}N_4O_2$.3HCl.4H$_2$O) C, H, N.

Example 9

N-(4-(4-(2-methoxyphenyl)piperazin-1-yl)-trans-but-2-enyl)-9H-fluorene-2-carboxamide (15). Prepared from 9H-fluorene-2-carboxylic acid and 4-(4-(2-methoxyphenyl)-piperazin-1-yl)-trans-but-2-enyl amine according to the general procedure. Yield: 61%. Mp. (hydrochloride): 224-226° C. $^1$H NMR (400 MHz, CDCl$_3$): d 2.68 (s, 4H), 3.09-3.10 (m, 6H), 3.86 (s, 3H), 3.94 (s, 2H), 4.13 (m, 2H), 5.81-5.83 (m, 2H), 6.32 (t, J 5.4, 1H), 6.85 (dd, J 8.2, 1.2, 1H), 6.89-6.96 (m, 2H), 7.00 (m, 1H), 7.35 (td, J 7.3, 1.3, 1H), 7.40 (td, J 7.4, 1.6, 1H), 7.57 (d, J 7.4, 1H), 7.78-7.83 (m, 3H), 7.99 (s, 1H). $^{13}$C NMR (101 MHz, CDCl$_3$): d 37.4, 42.0, 51.0, 53.8, 55.8, 60.8, 111.6, 118.7, 120.2, 121.0, 121.4, 123.4, 124.3, 125.7, 126.2, 127.5, 128.1, 129.3, 130.4, 133.1, 141.1, 141.7, 143.9, 144.5, 145.4, 152.7, 168.0. Anal. ($C_{29}H_{31}N_3O_2$.3HCl) C, H, N.

Example 10

N-(4-(4-(2,3-Dichlorophenyl)piperazin-1-yl)-3-hydroxybutyl)-4-pyridin-2-yl-benzamide (16). Prepared from 4-pyridin-2-yl-benzoic acid hydrochloride and 27a according to the general procedure. Yield: 52%. Mp. (hydrochloride): foam. $^1$H NMR (CDCl$_3$): δ 1.62 (m, 1H), 1.83 (m, 1H), 2.39-2.46 (m, 2H), 2.58 (m, 2H), 2.82 (m, 2H), 3.05 (s, 4H), 3.45 (m, 1H), 3.89 (m, 2H), 4.00 (s, 1H), 6.91 (dd, J 7.1, 2.5, 1H), 7.08-7.15 (m, 2H), 7.23 (ddd, J 5.89, 4.83, 2.58, 1H), 7.50 (dd, J 5.9, 3.7, 1H), 7.70-7.76 (m, 2H), 7.88 (d, J 8.3, 2H), 8.02 (d, J 8.3, 2H), 8.67 (dt, J 4.8, 1.2, 1H). $^{13}$C NMR (CDCl$_3$): δ 33.7, 38.8, 51.6, 53.5, 63.9, 66.6, 118.3, 120.5, 122.3, 124.3, 126.6, 127.1, 127.1, 133.6, 134.4, 136.4, 141.5, 149.3, 150.5, 155.7, 166.3. Anal. ($C_{26}H_{28}Cl_2N_4O_2$.2HCl.0.52-PrOH.1.5H$_2$O) C, H, N.

Example 11

N-(3-(4-(2,3-Dichlorophenyl)-piperazin-1-A-3-hydroxybutyl)-9H-fluorene-2-carboxamide (17). Prepared from 9H-fluorene-2-carboxylic acid and 27a according to the general procedure. Yield: 58%. Mp. (oxalate): 188-190° C. $^1$H NMR (oxalate, CDCl$_3$, 5% D$_2$O) δ 1.60-1.69 (1H, m), 1.83-1.87 (1H, m), 2.42-2.50 (2H, m), 2.61 (2H, m), 2.86-2.87 (2H, m), 3.07 (4H, s), 3.45-3.52 (1H, m), 3.87-3.94 (4H, m), 6.94-8.00 (10H, m). $^{13}$C NMR (oxalate, CDCl$_3$, 5% D$_2$O) δ 33.6, 37.2, 38.6, 51.6, 53.5, 63.9, 66.7, 118.8, 119.9, 120.8, 124.1, 125.0, 125.4, 126.0, 127.2, 127.7, 127.8, 127.8, 133.1, 134.3, 141.0, 143.6, 144.3, 145.0, 151.3, 167.4, 167.8. Anal. ($C_{28}H_{29}Cl_2N_3O_2$.(COOH)$_2$), C, H, N.

Example 12

N-(3-Hydroxy-4-(4-(2-methoxy-phenyl)-piperazin-1-yl)-butyl)-4-pyridin-2-yl-benzamide (18). Prepared from 4-pyridin-2-yl-benzoic acid hydrochloride and 27b according to the general procedure. Yield: 47%. Mp. (oxalate): foam. $^1$H NMR (CDCl$_3$): δ1.63 (m, 1H), 1.84 (m, 1H), 2.43 (m, 2H), 2.64 (m, 2H), 2.88 (m, 2H), 3.11 (s, 4H), 3.46 (m, 1H), 3.86 (s, 3H), 4.94 (m, 2H), 6.86 (dd, J 7.4, 1.2, 1H), 6.92-6.94 (m, 2H), 7.01 (m, 1H), 7.23 (m, ), 7.52 (dd, J 5.9, 3.7, 1H), 7.74-7.79 (m, 2H), 7.91 (d, J 8.3, 2H), 8.05 (d, J 8.3, 2H), 8.71 (dt, J 4.8, 1.2, 1H). $^{13}$C NMR (CDCl$_3$): δ 33.0, 38.3, 50.5, 53.2, 55, 63.5, 66.3, 110.9, 117.9, 120.6, 120.7, 122.4, 122.8, 126.7, 127.2, 134.6, 136.6, 140.8, 141.7, 149.6, 152.0, 156.1, 166.7. Anal. ($C_{27}H_{32}N_4O_2$.2(COOH)$_2$.0.5H$_2$O) C, H, N.

Example 13

N-(3-Hydroxy-4-(4-(2-methoxyphenyl)piperazin-1-yl)-butyl)-9H-fluorene-2-carboxamide (19). Prepared from 9H-fluorene-2-carboxylic acid and 27b according to the general procedure. Yield: 45%. Mp. (oxalate): foam. ($^1$H NMR (CDCl$_3$): δ 1.64 (m, 1H), 1.83 (m, 1H), 2.43 (m, 2H), 2.87 (m, 2H), 3.10 (s, 4H), 3.47 (m, 1H), 3.86 (s, 3H), 3-89-3.99 (m, 6H), 6.86 (d, J 7.4, 1H), 6.91-6.94 (m, 2H), 7.01 (m, 1H), 7.32-7.41 (m, 2H), 7.45 (dd, J 5.9, 3.5, 1H), 7.55 (d, J 7.4, 1H), 7.77-7.83 (m, 3H), 8.00 (s, 1H). $^{13}$C NMR (CDCl$_3$): δ 33.3, 36.9, 38.5, 50.7, 55.3, 63.8, 66.6, 111.1, 118.1, 119.6, 120.5, 120.9, 123.1, 123.8, 125.2, 125.8, 126.9, 127.5, 133.0, 140.7, 141.0, 143.3, 144.0, 144.6, 152.2, 167.5. Anal. ($C_{29}H_{33}N_3O_3$.(COOH)$_2$H$_2$O) C, H, N.

Example 14

1-(4-(2,3-Dichlorophenyl)piperazin-1-yl)-4-(4-(pyridin-2-yl)-benzamido)-butan-2-yl acetate (20). A solution of 16 (0.25 g, 0.5 mmol) in 10 mL of CH$_2$Cl$_2$ was treated with 70 μL (0.75 mmol) acetic anhydride followed by 140 μL (1.0 mmol) triethylamine. After stirring for 16 h, the mixture was washed with sodium bicarbonate solution, dried with sodium sulphate and purified by flash chromatography. Yield: 0.22 g (82%). Mp. (oxalate): foam. $^1$H NMR (CDCl$_3$): δ 1.84 (m, 1H), 2.05 (m, 2H), 2.12 (s, 3H), 2.52 (dd, J 13.2, 5.2, 1H), 2.65 (m, 5H), 2.99 (s, 4H), 3.25 (dq, J 9.7, 5.00, 1H), 3.81 (dt, J 12.3, 5.7, 1H), 5.19 (m, 1H), 6.89 (dd, J 7.7, 1.8, 1H), 7.06-7.17 (m, 3H), 7.26 (ddd, J 6.1, 4.8, 2.44, 1H), 7.73-7.76 (m, 2H), 7.93 (d, J 8.6, 2H), 8.07 (d, J 8.6, 2H), 8.70 (td, J 4.83, 1.50, 1.50, 1H). $^{13}$C NMR (CDCl$_3$): δ 21.0, 32.4, 36.1, 51.3, 53.7, 61.5, 69.6, 118.6, 120.8, 122.7, 124.5, 127.0, 127.4, 127.5, 133.9, 134.7, 136.9, 142.1, 149.8, 151.1, 156.2, 167.1, 171.5, Anal. (C$_{26}$H$_{30}$Cl$_2$N$_4$O$_3$.1.5(COOH)$_2$.H$_2$O) C, H, N.

Example 15

N-(4-(4-(2,3-Dichlorophenyl)piperazin-1-yl)-2-hydroxybutyl)-4-(pyridin-2-yl)-benzamide (21). Prepared from 4-pyridin-2-yl-benzoic acid and 30a according to the general procedure. Yield: 52%. Mp. (oxalate): foam. $^1$H NMR (CDCl$_3$): δ 1.63 (ddd, J 14.6, 6.0, 3.4, 1H), 1.81 (dtd, J 14.5, 10.9, 10.8, 3.9, 1H), 2.72 (m, 6H), 3.07 (s, 4H), 3.34 (ddd, J 13.4, 7.6, 4.6, 1H), 3.77 (ddd, J 13.4, 6.7, 3.4, 1H), 4.07 (m, 1H), 6.77 (t, J 5.3, 1H), 6.93 (dd, J 7.4, 2.2, 1H), 7.13-7.19 (m, 2H), 7.28 (m, 1H), 7.76-7.81 (m, 2H), 7.91 (d, J 8.6, 2H), 8.07 (d, J 8.6, 2H), 8.72 (td, J 4.8, 1.4, 1.4, 1H). $^{13}$C NMR (CDCl$_3$): δ 28.8, 45.8, 51.4, 53.3, 57.5, 72.7, 118.7, 120.9, 122.8, 125.0, 127.1, 127.5, 127.6, 127.7, 134.2, 134.8, 137.0, 142.2, 149.9, 150.9, 156.3, 167.3. Anal, (C$_{26}$H$_{28}$Cl$_2$N$_4$O$_2$.(COOH)$_2$H$_2$O), C, H, N.

Example 16

N-(4-(4-(2,3-Dichlorophenyl)piperazin-1-yl)-2-hydroxybutyl)-9H-fluorene-2-carboxamide (22). Prepared from 9H-fluorene-2-carboxylic acid and 30a according to the general procedure. Yield: 68%. Mp. (oxalate): foam. $^1$H NMR (CDCl$_3$): δ 1.63 (m, 1H), 1.78 (m, 1H), 2.63 (s, 2H), 2.72-2.84 (m, 2H), 2.87 (s, 2H), 3.07 (s, 4H), 3.34 (m, 1H), 3.77 (ddd, 13.7, 7.0, 3.5, 1H), 3.94 (s, 2H), 4.07 (m, 1H), 6.90 (dd, J 5.4, 2.0, 1H), 7.12-7.18 (m, 2H), 7.36 (t, J 5.3, 1H), 7.37 (t, J 5.4, 1H), 7.41 (d, J 7.0, 1H), 7.81-7.82 (m, 3H), 8.00 (s, 1H). $^{13}$C NMR (CDCl$_3$): δ 28.9, 37.0, 45.9, 51.4, 53.4, 57.5, 72.8, 118.7, 119.8, 120.7, 124.0, 125.0, 125.3, 126.0, 127.1, 127.6, 127.7, 127.8, 133.0, 134.2, 140.8, 143.6, 144.2, 145.0, 150.9, 168.0. Anal. (C$_{28}$H$_{29}$Cl$_2$N$_3$O$_2$.2.5HCl.0.5EtOAc.1.75H$_2$O) C, H, N.

Example 17

N-(4-(4-(2-Methoxyphenyl)piperazin-1-yl)-2-hydroxybutyl)-9H-fluorene-2-carboxamide (23). Prepared from 9H-fluorene-2-carboxylic acid and 30b according to the general procedure. Yield: 42%. Mp. (oxalate): foam. $^1$H NMR (CDCl$_3$): δ 1.62 (ddd, J 9.9, 6.1, 3.4, 1H), 1.80 (m, 1H), 2.63 (s, 2H), 2.76 (m, 2H), 2.88 (s, 2H), 3.10 (s, 4H), 3.33 (ddd, J 13.4, 7.7, 4.5, 1H), 3.78 (ddd, J 13.4, 6.8, 3.4, 1H), 3.80 (s, 3H), 3.91 (s, 2H), 4.06 (m, 1H), 6.83-6.87 (m, 2H), 6.89-6.92 (m, 2H), 7.01 (ddd, J 8.0, 5.8, 3.3, 1H), 7.34 (td, J 7.4, 1.3, 1H), 7.39 (td, J 7.5, 1.3, 1H), 7.55 (d, J 7.5, 1H), 7.79 (dd, J 7.9, 0.5, 1H), 7.82 (dd, J 8.1, 1.5, 1H), 8.00 (d, J 0.7, 1H). $^{13}$C NMR (CDCl$_3$): δ 28.8, 36.9, 45.8, 50.6, 53.5, 55.4, 57.4, 72.6, 111.2, 118.2, 119.7, 120.6, 121.0, 123.2, 123.9, 125.2, 125.9, 127.0, 127.6, 132.9, 140.7, 140.8, 143.4, 144.0, 144.8, 152.2, 167.9. Anal. (C$_{29}$H$_{33}$N$_3$O$_3$.(COOH)$_2$.1.25H$_2$O) C, H, N.

Example 18

2-(Oxiran-2-yl)-ethyl-isoindoline-1,3-dione (25). A suspension of 1.84 g (10.0 mmol) phthalimid potassium salt in 20 mL DMF was treated with 2.27 g (15.0 mmol) 24 in the microwave (pressure vessel, P$_{max}$ 150 W, cooling, 100° C., 20 min). See *J. Org. Chem.* 1969, 34, 4060-4065. The cooled reaction mixture was filtered, diluted with EtOAc (20 mL) and was washed with H$_2$O (2×10 mL). The organic phase was dried with sodium sulphate and the volatiles were removed in vacuo to give 25 (1.68 g, 78%) as a foam, which was used without further purification. $^1$H NMR (CDCl$_3$): δ 1.86 (m, 1H), 2.00 (m, 1H), 2.46 (m, 1H), 2.73 (t, J 3.9, 1H), 3.00 (m, 1H), 3.89 (m, 2H), 7.70-7.74 (m, 2H), 7.83-7.87 (m, 2H). $^{13}$C NMR (CDCl$_3$): δ 31.7, 35.2, 46.5, 50.4, 123.4, 132.2, 134.1, 168.4.

Example 19

2-(4-(4-(2,3-Dichlorophenyl)-piperazin-1-yl)-3-hydroxybutyl)-isoindoline-1,3-dione (26a). A sample of 2.1 g (9.0 mmol) 1-(2,3-dichlorophenyl)-piperazine in 40 mL 2-PrOH was reacted in the microwave (pressure vessel, P$_{max}$ 150 W, cooling, 90° C., 20 min) with 2.0 g (9.0 mmol) 25. The solvent was removed in vacuo and the foamy residue was washed with 10 mL 2-PrOH. Yield: 2.96 g (73%). $^1$H NMR (CDCl$_3$): δ 1.79 (m, 2H), 2.42 (m, 2H), 2.56 (s, 2H), 2.79 (m, 2H), 3.02 (s, 4H), 3.60 (s, 1H), 3.74-3.83 (m, 3H), 6.90 (m, 1H), 7.06-7.11 (m, 2H), 7.67 (m, 2H), 7.81 (m, 2H). $^{13}$C NMR (CDCl$_3$): δ 33.9, 35.3, 51.4, 53.4, 63.8, 64.5, 118.2, 122.7, 124.1, 127.0, 131.6, 133.4, 133.4, 150.4, 167.7.

Example 20

2-(4-(4-(2-Methoxyphenyl)piperazin-1-yl)-3-hydroxybutyl)isoindoline-1,3-dione (26b). Prepared from 1-(2-methoxyphenyl)piperazine and 25 in a similar fashion as described above for 26a. Yield: 28%. Mp.: 192-194° C. $^1$H NMR (CDCl$_3$): δ 1.79 (q, J 6.8, 2H), 2.41 (m, 2H), 2.61 (s, 2H), 2.85 (s, 2H), 3.07 (s, 4H), 3.77 (m, 1H), 3.85 (s, 3H), 3.91 (m, 2H), 6.86 (d, J 7.0, 1H), 6.91-6.95 (m, 2H), 7.00 (m, 1H), 7.85 (dd, J 5.5, 3.0, 2H), 7.71 (dd, J 5.4, 3.1, 2H). $^{13}$C NMR (CDCl$_3$): δ 33.8, 35.4, 50.9, 53.6, 55.6, 64.1, 64.7, 111.3, 118.4, 121.2, 123.2, 123.4, 132.4, 134.1, 141.4, 152.4.

Example 21

4-Amino-1-(4-(2,3-dichlorophenyl)piperazin-1-yl-butan-2-ol (27a). A sample of 4.48 g (10.0 mmol) 26a was fully dissolved in 25 mL EtOH and treated with 0.48 g (15.0 mmol) hydrazine in the microwave (pressure vessel, P$_{max}$ 150 W, cooling, 90° C., 20 min). The cooled reaction mixture was filtered and the filtrate was evaporated in vacuo. Both the residue from the evaporation and the initial precipitate were partitioned between CHCl$_3$ and 20% potassium carbonate solution. The layers were separated and the aqueous layer was dried with sodium sulphate to give the title compound as an oil, which was used without further purification. Yield: 2.25 g (71%). $^1$H NMR (CDCl$_3$): δ 1.56 (m, 2H), 2.40 (m, 2H), 2.61 (s, 2H), 2.80 (s, 2H), 2.97-3.05 (m, 9H), 3.89 (m, 1H), 6.92 (dd, J 6.3, 3.1, 1H), 7.09-7.14 (m, 2H). $^{13}$C NMR (CDCl$_3$): δ 37.4, 39.7, 51.5, 53.6, 64.5, 66.3, 118.3, 124.2, 127.1, 133.5, 150.6.

Example 22

4-Amino-1-(4-(2-methoxy-phenyl)-piperazin-1-yl)-butan-2-ol (27b). Prepared from 26b in a similar fashion as described above for 27a. Yield: 69%. Wax. $^1$H NMR (CDCl$_3$): δ 1.59 (m, 2H), 2.41 (m, 2H), 2.57 (m, 2H), 2.79-2.81 (m, 9H), 3.86 (s, 3H), 3.91 (m, 1H), 6.86 (d, J 7.5, 1H), 6.91-6.96 (m, 2H), 6.98-7.03 (m, 1H). $^{13}$C NMR (CDCl$_3$): δ 37.3, 39.7, 50.9, 53.6, 55.5, 64.5, 66.2, 111.2, 118.3, 121.1, 123.1, 141.3, 152.3.

Example 23

1-(2,3-Dichlorophenyl)-4-(2-(oxiran-2-yl)ethyl)piperazine (28a). 2.31 g (10.0 mmol) 1-(2,3-dichlorophenyl)piperazine was added to a suspension of 2.27 g (15.0 mmol) 24, 4.15 g (30.0 mmol) potassium carbonate in 150 mL acetone and the reaction mixture was refluxed for 24 h. The reaction mixture was filtered and the volatiles were removed in vacuo to give an oil (2.86 g, 95%), which was used without further purification. $^1$H NMR (CDCl$_3$): δ 1.72 (m, 1H), 1.83 (m, 1H), 2.53 (dd, J 5.0, 2.7, 1H), 2.61 (ddd, J 8.3, 6.5, 3.0, 2H), 2.66 (s, 4H), 2.79 (dd, J 4.9, 4.0, 1H), 3.01 (m, 1H), 3.07 (s, 4H), 6.96 (dd, J 6.5, 3.1, 1H), 7.11-7.19 (m, 2H). $^{13}$C NMR (CDCl$_3$): δ 30.2, 47.1, 51.0, 51.4, 53.3, 55.0, 118.6, 124.6, 127.5, 134.0, 151.3.

Example 24

1-(2-Methoxyphenyl)-4-(2-(oxiran-2-yl)ethyl)piperazine (28b). Prepared from 24 and 1-(2-methoxyphenyl)piperazine in a similar fashion as described above for 28a. Yield: 87%, $^1$H NMR (CDCl$_3$): δ 2.60 (m, 2H), 2.67 (s, 4H), 2.78 (dd, J 4.9, 4.0), 3.00 (m, 1H), 3.10 (s, 4H), 3.86 (s, 3H), 6.86 (dd, J 7.8, 1.3, 1H), 6.88-7.03 (m, 3H). $^{13}$C NMR (CDCl$_3$): δ 30.2, 47.2, 50.7, 51.0, 53.5, 55.2, 55.4, 111.2, 118.3, 121.1, 123.0, 141.4, 152.3.

Example 25

1-Azido-4-(4-(2,3-dichlorophenyl)piperazin-1-yl)butan-2-ol (29a). A suspension of 0.75 g (2.5 mmol), 0.24 g (3.8 mmol) sodium azide and 0.27 g (5.0 mmol) ammonium chloride in 5 mL DMF was heated at 100° C. for 5 h. The reaction mixture was partitioned between 10 mL CHCl$_3$ and 10 mL H$_2$O. The aqueous organic layer was extracted twice with 10 mL CHCl$_3$, dried over sodium sulphate and the volatiles were removed in vacuo. The residue was purified by flash chromatography to give the 29a as an oil. Yield: 0.44 g (51%). $^1$H NMR (CDCl$_3$): δ 1.56 (ddd, J 14.7, 6.5, 3.4, 1H), 1.81 (m, 1H), 2.62 (s, 2H), 2.75 (m, 2H), 2.87 (s, 2H), 3.07 (s, 4H), 3.27 (dd, J 5.1, 1.4, 2H), 4.04 (dtd, J 7.9, 5.3, 2.6, 1H), 6.52 (s, 1H), 6.93 (dd, J 7.2, 2.4, 1H), 7.12-7.19 (m, 21-1). $^{13}$C NMR (CDCl$_3$): δ 28.4, 51.3, 53.3, 56.5, 57.3, 73.0, 118.7, 124.9, 127.6, 134.1, 150.9.

Example 26

1-Azido-4-(4-(2-methoxyphenyl)piperazin-1-yl)butan-2-ol. Prepared from 28b in a similar fashion as described above for 29a. Yield: 15%, $^1$H NMR (CDCl$_3$): δ 1.55 (ddd, J 14.6, 6.7, 3.6, 1H), 1.80 (m, 1H), 2.62 (s, 2H), 2.74 (m, 2H), 2.89 (s, 2H), 3.09 (s, 4H), 3.24 (dd, J 11.6, 4.1, 1H), 3.29 (dd, J 11.6, 4.9, 1H), 3.86 (s, 3H), 4.03 (dtd, J 9.8, 5.5, 2.5, 1H), 6.86 (d, J 8.0, 1H), 6.89-6.95 (m, 2H), 7.01 (ddd, J 8.0, 5.1, 4.1, 1H), $^{13}$C NMR (CDCl$_3$): δ 28.4, 50.7, 53.5, 53.5, 55.4, 56.6, 57.4, 73.0, 111.2, 118.3, 121.1, 123.2, 140.9, 152.3.

Example 27

1-Amino-4-(4-(2,3-dichlorophenyl)piperazin-1-yl)butan-2-ol (30a). A solution of 29a (0.41 g, 1.2 mmol) and 1.87 g (7.2 mmol) triphenylphosphine in 20 mL of a THF/H$_2$O mixture (10:1 v/v) was stirred at room temperature for 16 h. The volatiles were removed in vacuo and the residue was taken up in 2-PrOH (5 mL) and treated with ethereal hydrochloric acid to give desired amine as a hydrochloride (0.33 g, 77%). $^1$H NMR (CDCl$_3$): δ 1.53 (ddd, J 14.5, 6.8, 4.0, 1H), 1.71 (m, 1H), 2.61 (s, 2H), 2.65-2.77 (m, 4H), 2.84 (s, 2H), 3.07 (m, 4H), 3.77 (m, 1H), 6.93 (dd, J 7.0, 2.5, 1H), 7.12-7.17 (m, 2H). $^{13}$C NMR (CDCl$_3$): δ 29.0, 48.3, 51.3, 53.3, 74.9, 118.6, 124.8, 127.5, 134.0, 150.9.

Example 28

1-Amino-4-(4-(2-methoxyphenyl)piperazin-1-yl)butan-2-ol (30b). Prepared from 29b in a similar fashion as described above for 30a. Yield: 13%. $^1$H NMR (CDCl$_3$): δ 1.52 (ddd, J 14.5, 6.5, 3.9, 1H), 1.71 (m, 1H), 2.54-2.77 (m, 4H), 2.86 (s, 2H), 3.09 (s, 4H), 3.77 (m, 1H), 3.87 (s, 3H), 6.86 (d, J 7.9, 1H), 6.90-6.95 (m, 2H), 7.00 (m, 1H). $^{13}$C NMR (CDCl$_3$): δ 29.0, 48.4, 50.7, 53.6, 55.4, 57.6, 75.2, 111.2, 118.3, 121.1, 123.2, 141.0, 152.3.

TABLE 1

| | | | | D3 K$_i$ [nM] | | | | | |
|---|---|---|---|---|---|---|---|---|---|
| Compd. | structure | D2 | SEM | | SEM | D4 | SEM | D2/D3 | D4/D2 |
| 9 | 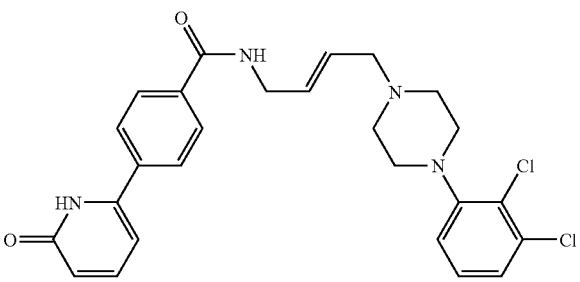 [SMILES: O=C(NC/C=C/CN1CCN(c2cccc(Cl)c2Cl)CC1)c1ccc(-c2cccc(=O)[nH]2)cc1] | 23.6 | 5.7 | 0.6 | 0.1 | | | 39 | |

TABLE 1-continued
Human D$_2$-like Family Receptor Subtype Binding Data in HEK Cells
| Compd. | structure | D2 | SEM | D3 K$_i$ [nM] | SEM | D4 | SEM | D2/D3 | D4/D2 |
|---|---|---|---|---|---|---|---|---|---|
| 10 | 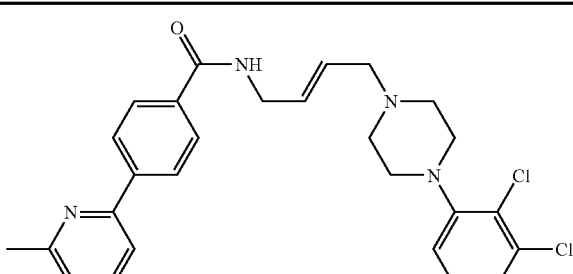 | 105 | 24 | 1.4 | 0.3 | | | 75 | |
| 11 | 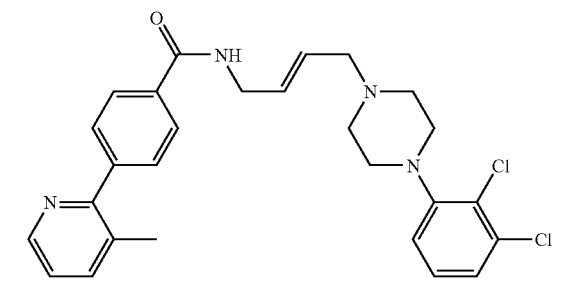 [SMILES: Cc1cccnc1-c1ccc(C(=O)NC/C=C/CN2CCN(c3cccc(Cl)c3Cl)CC2)cc1] | 92.0 | 9.4 | 1.6 | 0.4 | | | 58 | |
| 12 | 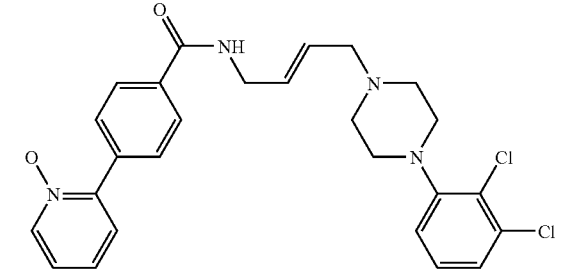 | 25.8 | 3.1 | 1.1 | 0.3 | | | 23 | |
| 13 | 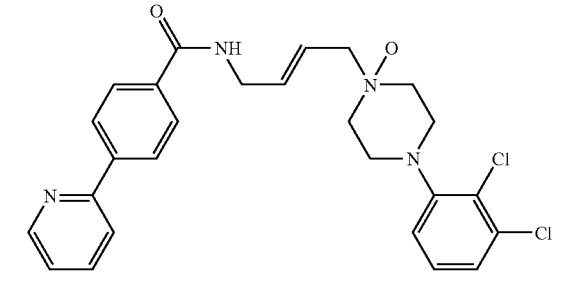 | 1160 | 230 | 49.2 | 9.3 | | | 24 | |
| 14 | 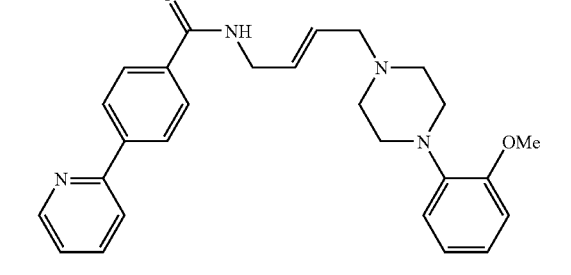 | 69.0 | 13 | 2.9 | 1.1 | | | 24 | |

TABLE 1-continued
Human D$_2$-like Family Receptor Subtype Binding Data in HEK Cells
| Compd. | structure | D2 | SEM | D3 K$_i$ [nM] | SEM | D4 | SEM | D2/ D3 | D4/ D2 |
|---|---|---|---|---|---|---|---|---|---|
| 15 | 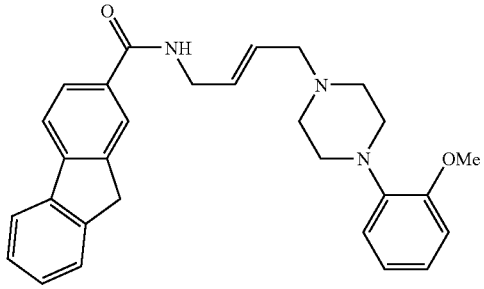 [SMILES: COc1ccccc1N1CCN(C/C=C/CNC(=O)c2ccc3c(c2)Cc2ccccc2-3)CC1] | 48.4 | 7.3 | 12 | 0.1 | | | 40 | |
| 16 | 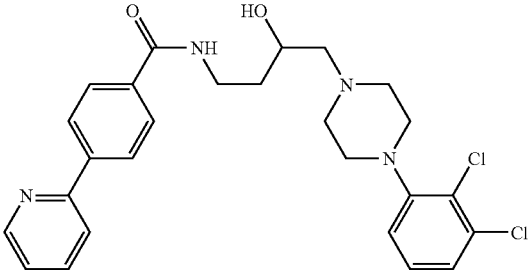 [SMILES: O=C(NCCC(O)CN1CCN(c2cccc(Cl)c2Cl)CC1)c1ccc(-c2ccccn2)cc1] | 267 | 20 | 3.0 | 0.2 | 4620 | 200 | 89 | 1540 |
| 17 | 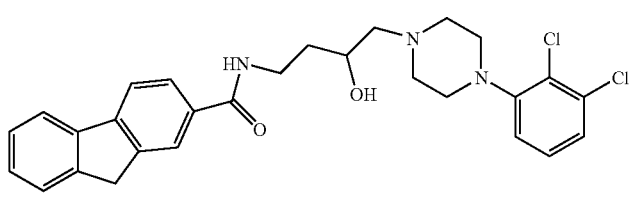 [SMILES: O=C(NCCC(O)CN1CCN(c2cccc(Cl)c2Cl)CC1)c1ccc2c(c1)Cc1ccccc1-2] | 319 | 54 | 1.8 | 0.0 | 16400 | 2600 | 177 | 9110 |
| 18 | 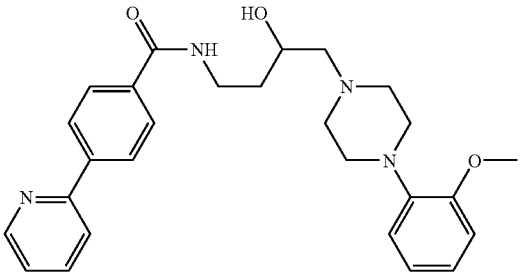 [SMILES: COc1ccccc1N1CCN(CC(O)CCNC(=O)c2ccc(-c3ccccn3)cc2)CC1] | 284 | 48 | 2.8 | 0.8 | 1490 | 150 | 101 | 532 |
| 19 | 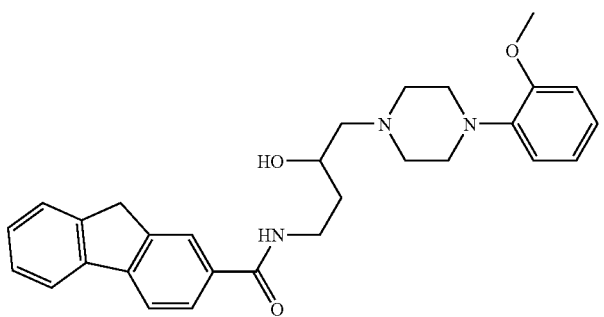 [SMILES: COc1ccccc1N1CCN(CC(O)CCNC(=O)c2ccc3c(c2)Cc2ccccc2-3)CC1] | 249 | 14 | 1.8 | 0.3 | 1230 | 330 | 138 | 683 |

TABLE 1-continued

Human D₂-like Family Receptor Subtype Binding Data in HEK Cells

| Compd. | structure | D2 | SEM | D3 $K_i$ [nM] | SEM | D4 | SEM | D2/ D3 | D4/ D2 |
|---|---|---|---|---|---|---|---|---|---|
| 20 | 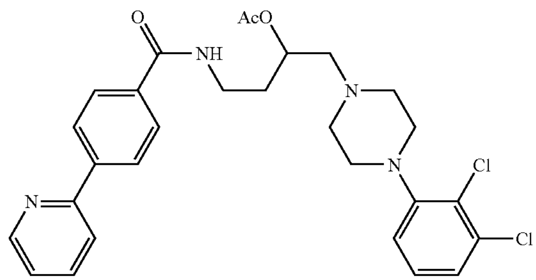 [SMILES: CC(=O)OC(CCNC(=O)c1ccc(-c2ccccn2)cc1)CN1CCN(c2cccc(Cl)c2Cl)CC1] | 134 | 28 | 11.7 | 1.0 | | | 11 | |
| 21 | 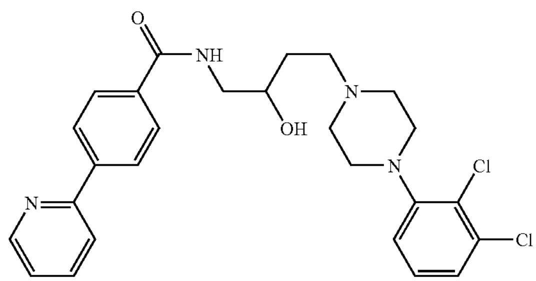 [SMILES: O=C(NCC(O)CCN1CCN(c2cccc(Cl)c2Cl)CC1)c1ccc(-c2ccccn2)cc1] | 28.4 | 6.4 | 0.5 | 0.1 | | | 57 | |
| 22 | 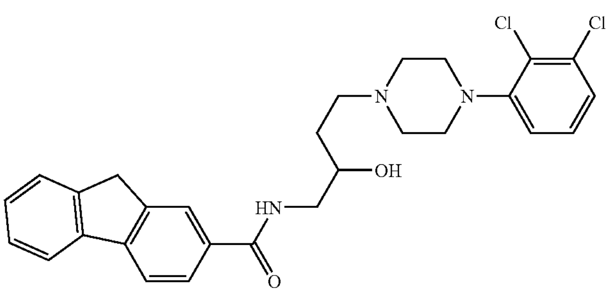 [SMILES: O=C(NCC(O)CCN1CCN(c2cccc(Cl)c2Cl)CC1)c1ccc2c(c1)Cc1ccccc1-2] | 84.0 | 5.3 | 2.5 | 0.3 | | | 34 | |
| 23 | 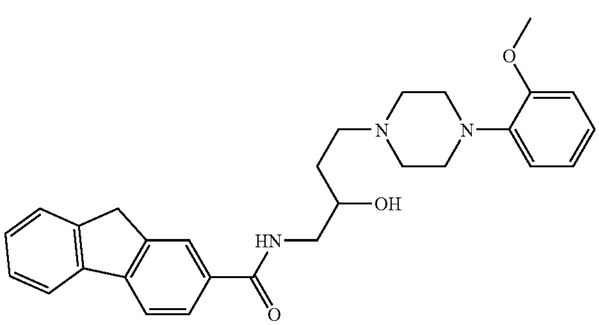 [SMILES: COc1ccccc1N1CCN(CCC(O)CNC(=O)c2ccc3c(c2)Cc2ccccc2-3)CC1] | 68.4 | 6.4 | 1.3 | 0.4 | | | 53 | |
| 34 | 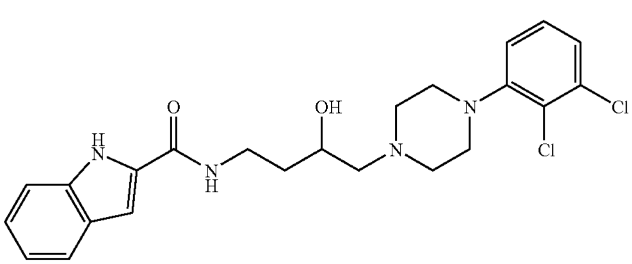 [SMILES: O=C(NCCC(O)CN1CCN(c2cccc(Cl)c2Cl)CC1)c1cc2ccccc2[nH]1] | 200 | 52 | 0.9 | 0.3 | | | 225 | |

TABLE 1-continued

Human $D_2$-like Family Receptor Subtype Binding Data in HEK Cells

| Compd. | structure | D2 | SEM | D3 $K_i$ [nM] | SEM | D4 | SEM | D2/ D3 | D4/ D2 |
|---|---|---|---|---|---|---|---|---|---|
| 34 Enantiomer A | 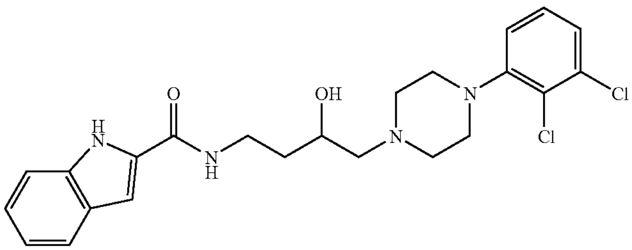 [SMILES: O=C(NCCC(O)CN1CCN(c2cccc(Cl)c2Cl)CC1)c1cc2ccccc2[nH]1] | 441 | 52 | 1.1 | 0.3 | | 400 | | |
| 34 Enantiomer B | 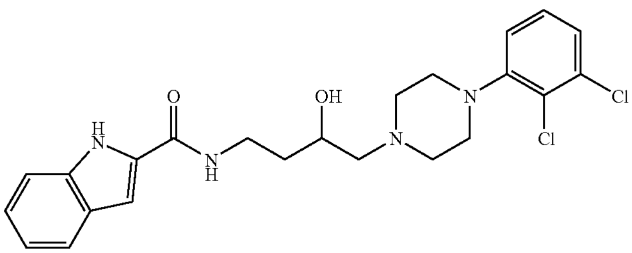 [SMILES: O=C(NCCC(O)CN1CCN(c2cccc(Cl)c2Cl)CC1)c1cc2ccccc2[nH]1] | 1083 | 379 | 16.5 | 3.2 | | 65 | | |
| 35 | 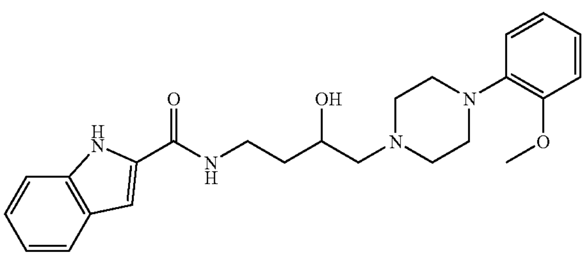 [SMILES: COc1ccccc1N1CCN(CC(O)CCNC(=O)c2cc3ccccc3[nH]2)CC1] | 248.6 | 62.7 | 1.37 | 0.2 | 1919 | 373 | 181 | 1401 |
| 36 | 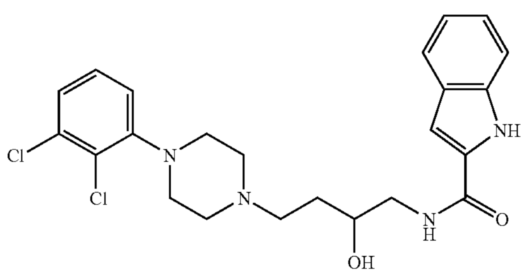 [SMILES: O=C(NCC(O)CCN1CCN(c2cccc(Cl)c2Cl)CC1)c1cc2ccccc2[nH]1] | 28.4 | 6.5 | 0.26 | 0.06 | | | 109 | |
| 37 | 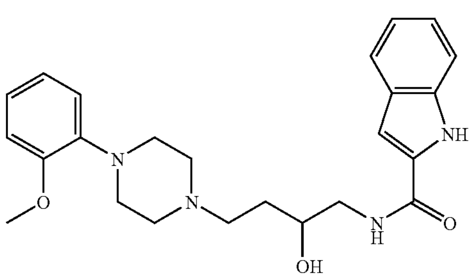 [SMILES: COc1ccccc1N1CCN(CCC(O)CNC(=O)c2cc3ccccc3[nH]2)CC1] | 52.5 | 4.5 | 0.5 | 0.03 | | | 105 | |

TABLE 1-continued
Human D$_2$-like Family Receptor Subtype Binding Data in HEK Cells
| Compd. | structure | D2 | SEM | D3 K$_i$ [nM] | SEM | D4 | SEM | D2/ D3 | D4/ D2 |
|---|---|---|---|---|---|---|---|---|---|
| 38 | 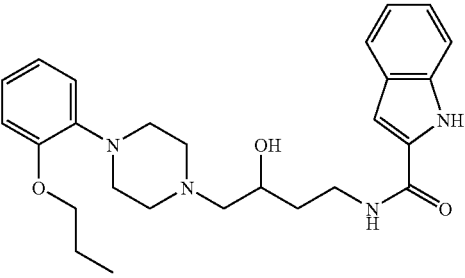 [SMILES: CCCOc1ccccc1N1CCN(CC(O)CCNC(=O)c2cc3ccccc3[nH]2)CC1] | 47.1 | 7.4 | 62.1 | 3.1 | | | 1 | |
| 39 | 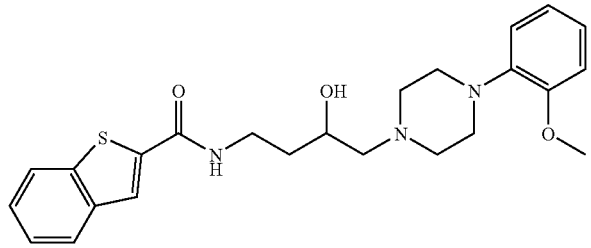 [SMILES: COc1ccccc1N1CCN(CC(O)CCNC(=O)c2cc3ccccc3s2)CC1] | 337 | 21.7 | 4.6 | 0.6 | | | 73 | |
| 42 | 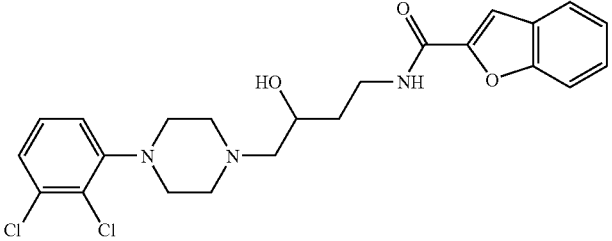 [SMILES: O=C(NCCC(O)CN1CCN(c2cccc(Cl)c2Cl)CC1)c1cc2ccccc2o1] | 185 | | 0.98 | | | | 188 | |
| 43 | 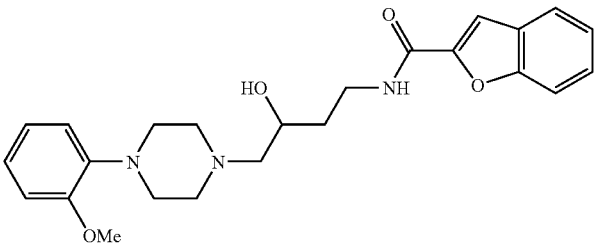 [SMILES: COc1ccccc1N1CCN(CC(O)CCNC(=O)c2cc3ccccc3o2)CC1] | 233 | | 5.4 | | | | 43 | |
| 44 | 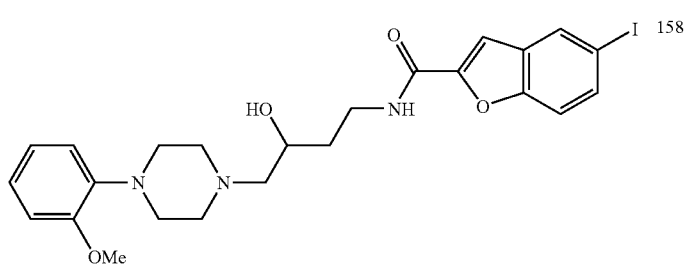 | 158 | | 2.2 | | | | 71 | |

TABLE 1-continued
Human D$_2$-like Family Receptor Subtype Binding Data in HEK Cells
| Compd. | structure | D2 | SEM | D3 K$_i$ [nM] | SEM | D4 | SEM | D2/ D3 | D4/ D2 |
|---|---|---|---|---|---|---|---|---|---|
| 45 | 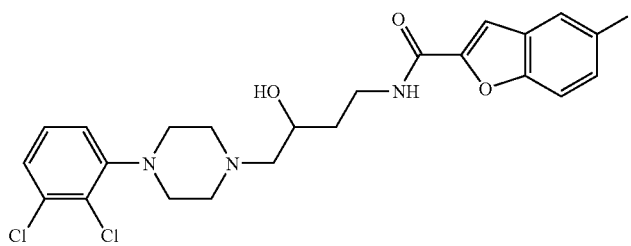 | 697 | | 3.5 | | | | 200 | |
| 46 | 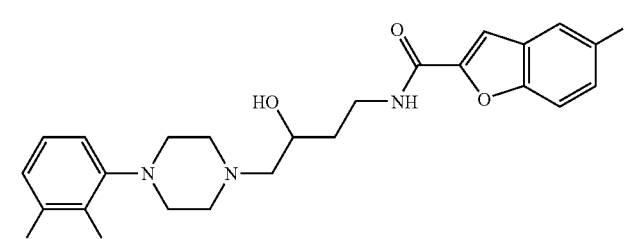 | 245 | | 1.6 | | | | 149 | |
| 47 | 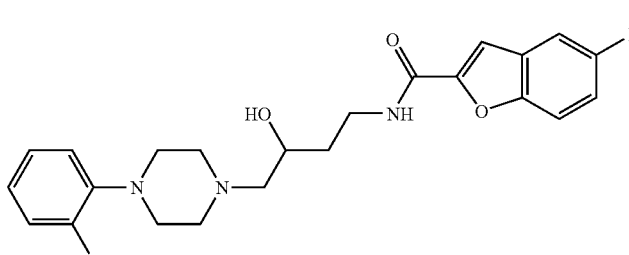 | 180 | | 0.65 | | | | 276 | |
| 48 | 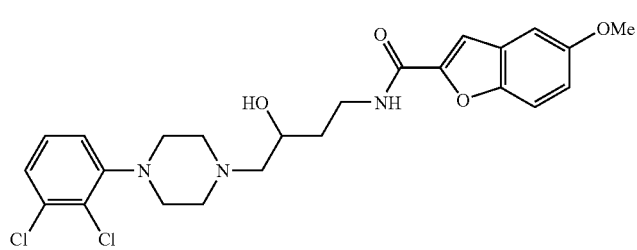 [SMILES: COc1ccc2oc(C(=O)NCCC(O)CN3CCN(c4cccc(Cl)c4Cl)CC3)cc2c1] | 244 | | 1.3 | | | | 185 | |
| 49 | 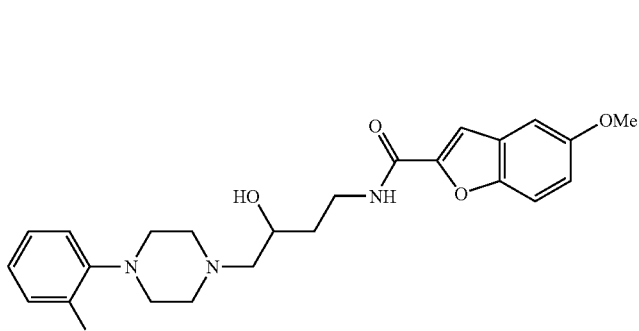 | 174 | | 1.0 | | | | 172 | |

TABLE 2

In Vitro Functional Data at D$_2$-like Family Receptor for selected ligands[a]

| Compd. | structure | IC$_{50}$ (nM) ± S.E.M. | |
| --- | --- | --- | --- |
| | | D2 | D3 |
| 9 | 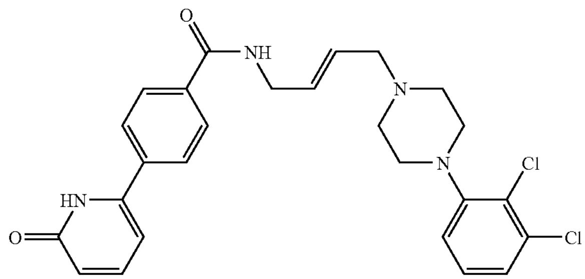 [SMILES: O=C(NC/C=C/CN1CCN(c2cccc(Cl)c2Cl)CC1)c1ccc(-c2cccc(=O)[nH]2)cc1] | 41 ± 8 | 1.0 ± 0.2 |
| 10 | 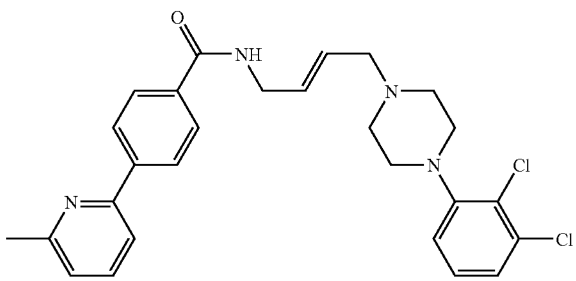 [SMILES: Cc1cccc(-c2ccc(C(=O)NC/C=C/CN3CCN(c4cccc(Cl)c4Cl)CC3)cc2)n1] | 1300 ± 320 | 6.7 ± 2.6 |
| 11 | 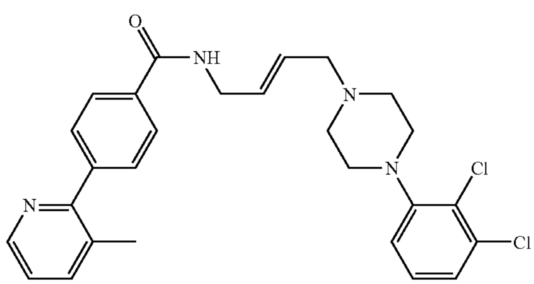 [SMILES: Cc1cccnc1-c1ccc(C(=O)NC/C=C/CN2CCN(c3cccc(Cl)c3Cl)CC2)cc1] | 368 ± 113 | 25.6 ± 8.5 |
| 12 | 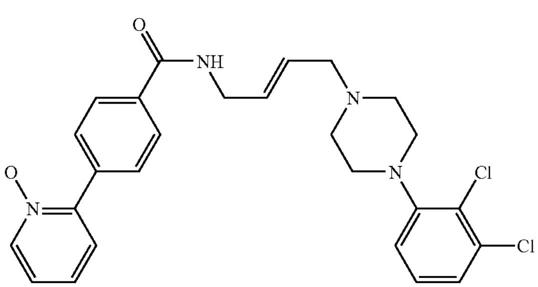 | 22.9 ± 2.0<br>231 ± 1 (31)[b] | 1.2 ± 0.0 |
| 14 | 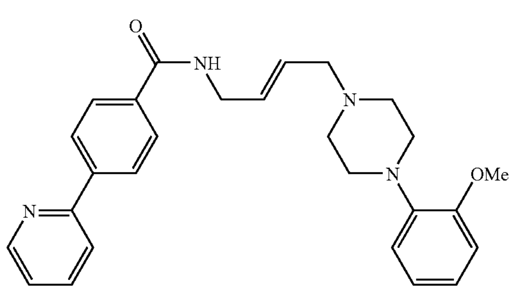 [SMILES: COc1ccccc1N1CCN(C/C=C/CNC(=O)c2ccc(-c3ccccn3)cc2)CC1] | 175 ± 17 | 42.6 ± 7.9 |

TABLE 2-continued

In Vitro Functional Data at D$_2$-like Family Receptor for selected ligands[a]

| Compd. | structure | IC$_{50}$ (nM) ± S.E.M. | |
| --- | --- | --- | --- |
| | | D2 | D3 |
| 15 | 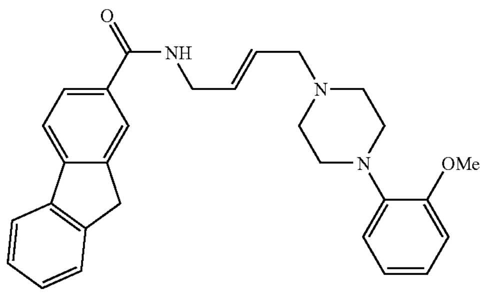 [SMILES: COc1ccccc1N1CCN(C/C=C/CNC(=O)c2ccc3c(c2)Cc2ccccc2-3)CC1] | 179 ± 48 | 18.9 ± 4.2 |
| 16 | 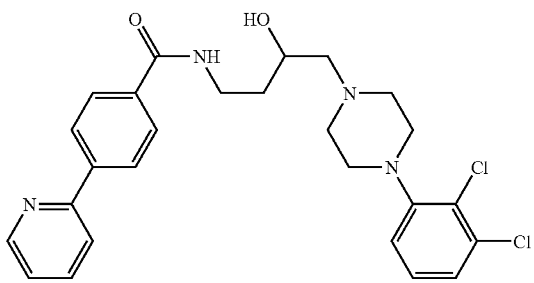 | 15.8 ± 2.7 (26)[b] | 1.0 ± 0.1 (48)[b] |
| 17 | 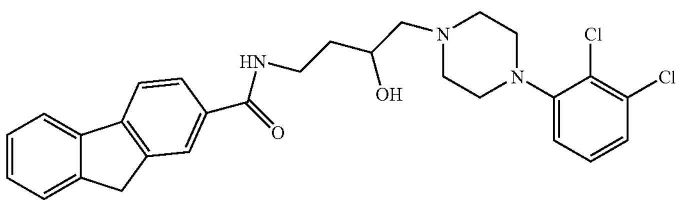 [SMILES: O=C(NCCC(O)CN1CCN(c2cccc(Cl)c2Cl)CC1)c1ccc2c(c1)Cc1ccccc1-2] | ND | 42.0 ± 1.3 (26)[b] |
| 18 | 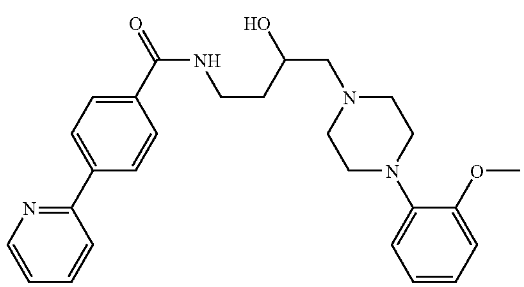 [SMILES: COc1ccccc1N1CCN(CC(O)CCNC(=O)c2ccc(-c3ccccn3)cc2)CC1] | ND | 12.8 ± 1.3 |
| 20 | 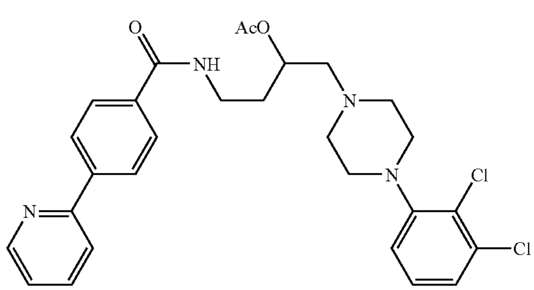 | ND | 3.9 ± 1.4 (47)[b] |

TABLE 2-continued

In Vitro Functional Data at D$_2$-like Family Receptor for selected ligands[a]

| Compd. | structure | IC$_{50}$ (nM) ± S.E.M. | |
| --- | --- | --- | --- |
| | | D2 | D3 |
| 21 | | 88.3 ± 15.7 | 5.4 ± 1.8 |
| | | | 3.4 ± 0.5 (20)[b] |

[a]Data were obtained through the NIDA Addiction Treatment Discovery Program contract with SRI (N01DA-1-8816).
[b]partial agonist activity: EC$_{50}$ (% stimulation)

TABLE 3

Binding affinities for a serotonin receptor subtypes for selected ligands.[a]

| Compd. | structure | 5HT$_{1A}$ | 5HT$_{2A}$ | 5HT$_{2c}$ | D$_3$ | 5HT$_{1A}$/D3 | 5HT$_{2A}$/D3 | 5HT$_{2c}$/D |
| --- | --- | --- | --- | --- | --- | --- | --- | --- |
| 9 | 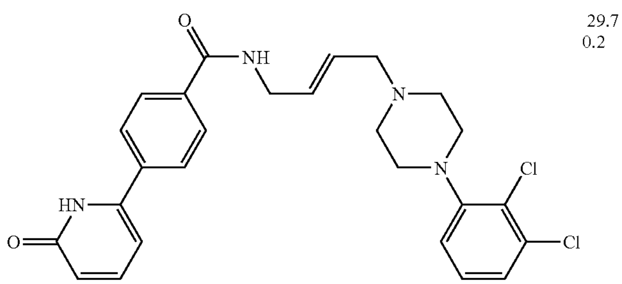 | 29.7 ± 0.2 | 15.5 ± 3.8 | 10.6 ± 0.0 | 0.6 ± 0.1 | 50 | 26 | 18 |
| 10 | 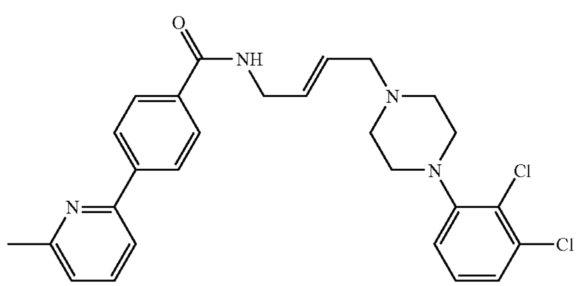 [SMILES: Cc1cccc(-c2ccc(C(=O)NC/C=C/CN3CCN(c4cccc(Cl)c4Cl)CC3)cc2)n1] | 309 ± 39 | 92.7 ± 16 | 96.4 ± 1.1 | 1.4 ± 0.3 | 221 | 66 | 69 |
| 11 | 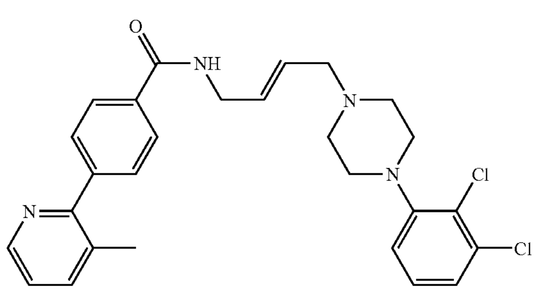 | 92 ± 8.3 | 46.9 ± 5.4 | 31 ± 2.3 | 1.6 ± 0.4 | 58 | 29 | 19 |

TABLE 3-continued
Binding affinities for a serotonin receptor subtypes for selected ligands.[a]
| Compd. | structure | 5HT$_{1A}$ | 5HT$_{2A}$ | 5HT$_{2c}$ | D$_3$ | 5HT$_{1A}$/D3 | 5HT$_{2A}$/D3 | 5HT$_{2c}$/D |
| --- | --- | --- | --- | --- | --- | --- | --- | --- |
| 12 | 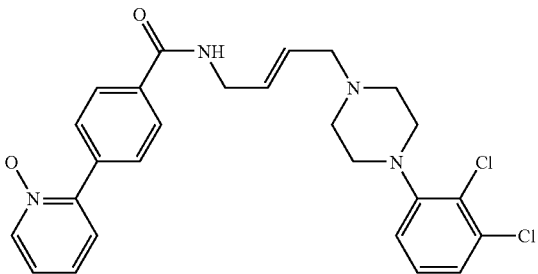 | 60.6 ± 4.3 | 57.9 ± 0.6 | 74.3 ± 3 | 1.1 ± 0.3 | 55 | 53 | 68 |
| 14 | 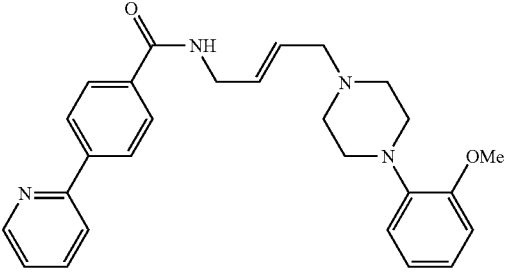 [SMILES: COc1ccccc1N1CCN(C/C=C/CNC(=O)c2ccc(-c3ccccn3)cc2)CC1] | 21.7 ± 3.5 | 75.3 ± 1.1 | 256 ± 33 | 2.9 ± 1.1 | 7 | 26 | 88 |
| 15 | 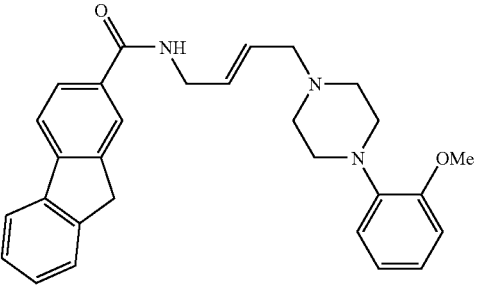 [SMILES: COc1ccccc1N1CCN(C/C=C/CNC(=O)c2ccc3c(c2)Cc2ccccc2-3)CC1] | 71.8 ± 2.1 | 65.7 ± 12 | 176 ± 14 | 1.2 ± 0.1 | 60 | 55 | 147 |
| 16 | 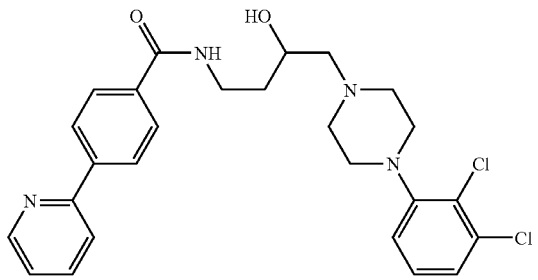 | 34.3 ± 0.3 | 42.3 ± 9.1 | 115 ± 20 | 3.0 ± 0.2 | 11 | 14 | 38 |
| 17 | 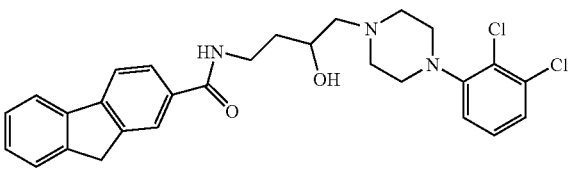 [SMILES: O=C(NCCC(O)CN1CCN(c2cccc(Cl)c2Cl)CC1)c1ccc2c(c1)Cc1ccccc1-2] | 1810 ± 350 | 545 ± 150 | 2830 ± 360 | 1.8 ± 0.0 | 1006 | 303 | 1572 |

TABLE 3-continued

Binding affinities for a serotonin receptor subtypes for selected ligands.[a]

| Compd. | structure | 5HT$_{1A}$ | 5HT$_{2A}$ | 5HT$_{2c}$ | D$_3$ | 5HT$_{1A}$/D3 | 5HT$_{2A}$/D3 | 5HT$_{2c}$/D |
|---|---|---|---|---|---|---|---|---|
| 18 | 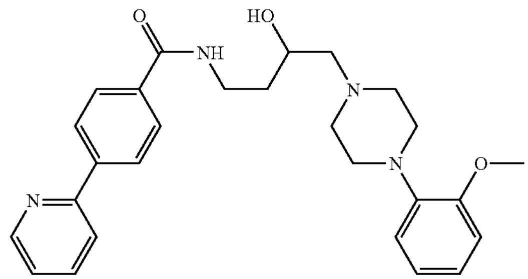 [SMILES: COc1ccccc1N1CCN(CC(O)CCNC(=O)c2ccc(-c3ccccn3)cc2)CC1] | 36.2 ± 7 | 695 ± 20 | 3940 ± 130 | 2.8 ± 0.8 | 13 | 248 | 1407 |
| 20 | 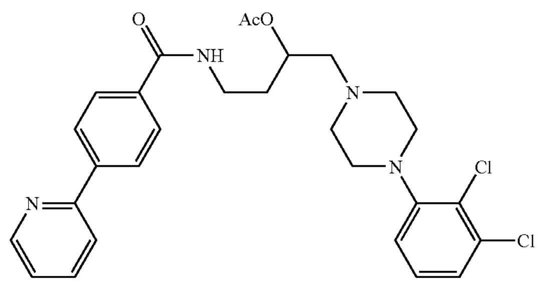 | 117 ± 12 | 88.7 ± 7.5 | 84.3 ± 5.3 | 11.7 ± 1.0 | 10 | 7 | 7 |
| 21 | 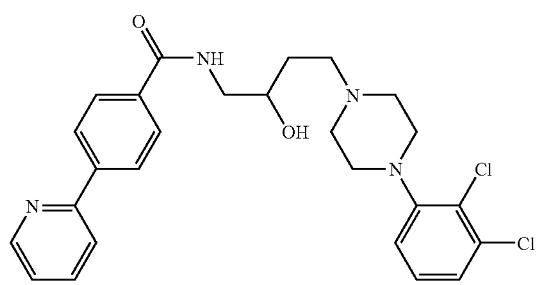 [SMILES: O=C(NCC(O)CCN1CCN(c2cccc(Cl)c2Cl)CC1)c1ccc(-c2ccccn2)cc1] | 15.1 ± 2.4 | 15.4 ± 2.8 | 25.2 ± 3.2 | 0.5 ± 0.1 | 30 | 31 | 50 |

[a]Data were obtained through the NIDA Addiction Treatment Discovery Program contract with SRI (N01DA-1-8816).

We claim:

1. A chemical compound of the following chemical formula:

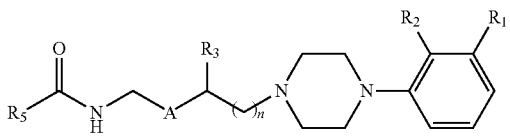

wherein:
A=CHR$_4$ or trans CH=CH;
n=0 or 1;
R$_1$ and R$_2$=independently represent hydrogen, halogen, or alkoxy;
R$_3$ and R$_4$=H, OH, OAc, alkoxy, halogen, amino, nitro, alkyl having from 2-8 carbons, or pyridyl;
R$_5$=phenyl, indole, thiophene, benzofuran, fluorenyl, or 2-pyridylphenyl; and R$_5$ is optionally substituted with one or more of hydrogen, halogen, amino, nitro, hydroxyl, alkoxy, alkyl, and pyridyl, substitution may occur at any of the ortho, meta, or para positions;
including all enantiomers and pharmaceutical salts thereof, wherein alkyl is a branched or unbranched, saturated or unsaturated, monovalent hydrocarbon radical having from 1-8 carbons, optionally substituted with one or more C$_1$ to C$_3$ alkyl, halogen, hydroxyl, amino, alkoxyl, or mercapto groups, and
wherein alkoxy is —OR group, wherein R is a C$_1$ to C$_3$ alkyl optionally substituted with one or more C$_1$ to C$_3$ alkyl, halogen, hydroxyl, amino, alkoxyl, or mercapto groups;
wherein when A=trans CH=CH, then R$_3$=OH, OAc, alkoxy, halogen, amino, nitro, alkyl, or pyridyl; and
wherein when A=CHR$_4$, then one of R$_3$ or R$_4$=OH, OAc, alkoxy, halogen, amino, nitro, alkyl, or pyridyl.

2. The chemical compound of claim 1 in which A is CHR$_4$.

3. The chemical compound of claim 1 that is: N-(3-hydroxy-4-(4-(2-methoxyphenyl)-piperazin-1-yl)-butyl)-4-pyridin-2-yl-benzamide.

4. The chemical compound of claim 1 that is: N-(3-hydroxy-4-(4-(2-methoxyphenyl)piperazin-1-yl)-butyl)-9H-fluorene-2-carboxamide.

5. The chemical compound of claim 1 that is: N-(4-(4-(2,3-dichlorophenyl)piperazin-1-yl)-3-hydroxybutyl)-1H-indole-2-carboxamide.

6. The chemical compound of claim 1 that is: N-(3-hydroxy-4-(4-(2-methoxyphenyl)piperazin-1-yl)butyl)-1H-indole-2-carboxamide.

7. The chemical compound of claim 1 that is: N-(4-(4-(2,3-dichlorophenyl)piperazin-1-yl)-3-hydroxybutyl)-5-iodobenzofuran-2 carboxamide or N-(4-(4-(2,3-dichlorophenyl)piperazin-1-yl)-3-hydroxybutyl)-5-fluorobenzo furan-2 carboxamide.

8. The chemical compound of claim 1 that is: 5-fluoro-N-(3-hydroxy-4-(4-(2-methoxyphenyl)piperazin-1-yl)butyl)-1H-indole-2-carboxamide.

9. The chemical compound of claim 1, wherein $R_3$=OH, OAc, alkoxy, halogen, amino, nitro, alkyl having from 2-8 carbons, or pyridyl.

10. The chemical compound of claim 1, wherein $R_4$=OH, OAc, alkoxy, halogen, amino, nitro, alkyl having from 2-8 carbons, or pyridyl.

11. The chemical compound of claim 1 that is: N-(4-(4-(2,3-dichlorophenyl)piperazin-1-yl)-3-hydroxybutyl)-5-methoxy-1H-indole-2-carboxamide.

12. The chemical compound of claim 1 that is: (R)—N-(4-(4-(2,3-dichlorophenyl)piperazin-1-yl)-3-hydroxybutyl)-1H-indole-2-carboxamide.

13. The chemical compound of claim 1 that is: (S)—N-(4-(4-(2,3-dichlorophenyl)piperazin-1-yl)-3-hydroxybutyl)-1H-indole-2-carboxamide.

14. The chemical compound of claim 1, wherein $R_3$=OH, OAc, alkoxy, halogen, amino, nitro, or pyridyl.

15. The chemical compound of claim 1, wherein $R_4$=OH, OAc, alkoxy, halogen, amino, nitro, or pyridyl.

16. The chemical compound of claim 1, wherein
A=$CHR_4$;
n=1;
$R_1$ and $R_2$=independently represent hydrogen, halogen, or alkoxy;
$R_3$=OH or halogen;
$R_4$=H; and
$R_5$=indole or fluorenyl, and $R_5$ is optionally substituted with alkoxy.

17. The chemical compound of claim 1, wherein
A=$CHR_4$;
n=1;
$R_1$ and $R_2$=Cl;
$R_3$=F;
$R_4$=H; and
$R_5$=indole or fluorenyl, and $R_5$ is optionally substituted with methoxy.

18. The chemical compound of claim 1, wherein
A=$CHR_4$;
n=1;
$R_1$=H;
$R_2$=methoxy;
$R_3$=OH;
$R_4$=H; and
$R_5$=indole substituted with methoxy.

* * * * *